Figure 11:
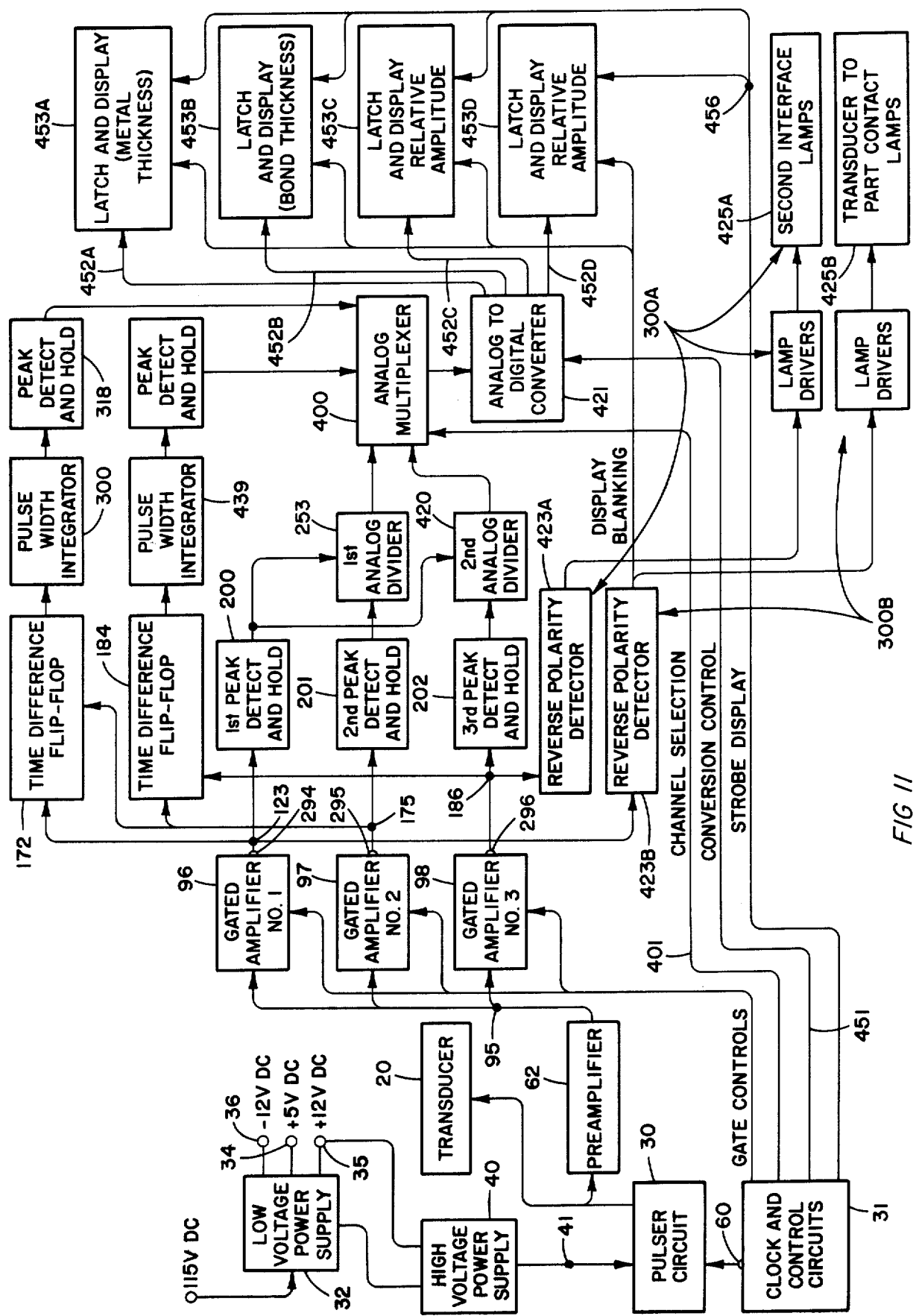

United States Patent [19]

Evans et al.

[11] 4,100,808

[45] Jul. 18, 1978

[54] APPARATUS FOR EVALUATING A BOND

[75] Inventors: Charles B. Evans, Arlington; John D. Fenton, Fort Worth; Bonner W. Staff, Grand Prairie, all of Tex.

[73] Assignee: Vought Corporation, Dallas, Tex.

[21] Appl. No.: 624,620

[22] Filed: Oct. 22, 1975

[51] Int. Cl.² ............................................. G01N 29/00
[52] U.S. Cl. .................................... 73/588; 73/612; 73/615
[58] Field of Search ............... 73/67, 67.8 R, 67.7, 73/67.9, 67.2

[56] References Cited

U.S. PATENT DOCUMENTS

| 2,846,874 | 8/1958 | Horn | 73/67.8 R |
| 2,903,886 | 9/1959 | Renault | 73/67.8 R |
| 3,014,364 | 12/1961 | Crooks | 73/67.8 R |
| 3,016,735 | 1/1962 | Arnold | 73/67.2 |
| 3,335,602 | 8/1967 | Martner | 73/67.8 R |
| 3,564,903 | 2/1971 | Woodmansee | 73/67.2 |
| 3,576,126 | 4/1971 | Weighart | 73/67.9 |
| 3,640,122 | 2/1972 | Nusbickel | 73/67.9 |
| 3,813,926 | 6/1974 | Stubbeman | 73/67.9 |
| 3,924,454 | 12/1975 | McElroy | 73/67.8 R |

FOREIGN PATENT DOCUMENTS 838,922  6/1960  United Kingdom ............ 73/67.8 R

Primary Examiner—Richard C. Queisser
Assistant Examiner—Stephen A. Kreitman
Attorney, Agent, or Firm—James M. Cate

[57] ABSTRACT

Disclosed is an apparatus and method for evaluating a bond between first and second structures bonded together by an intermediate layer of adhesive. Apparatus is provided for transmitting a pulse of ultrasonic wave energy that has a duration at least as short as 1.5 wave cycles into the bonded structures whereby a first reflected pulse may be reflected from a first surface of the first structure, a second reflected pulse reflected from the layer of adhesive, and a third pulse possibly reflected from the surface of the second structure adjacent the adhesive layer. Circuits are provided for sensing the first, second, and third reflected pulses and for providing an indication of the quality of the bond by comparing the amplitudes of the reflected pulses and determining if the ratios lie within predetermined ranges.

22 Claims, 35 Drawing Figures

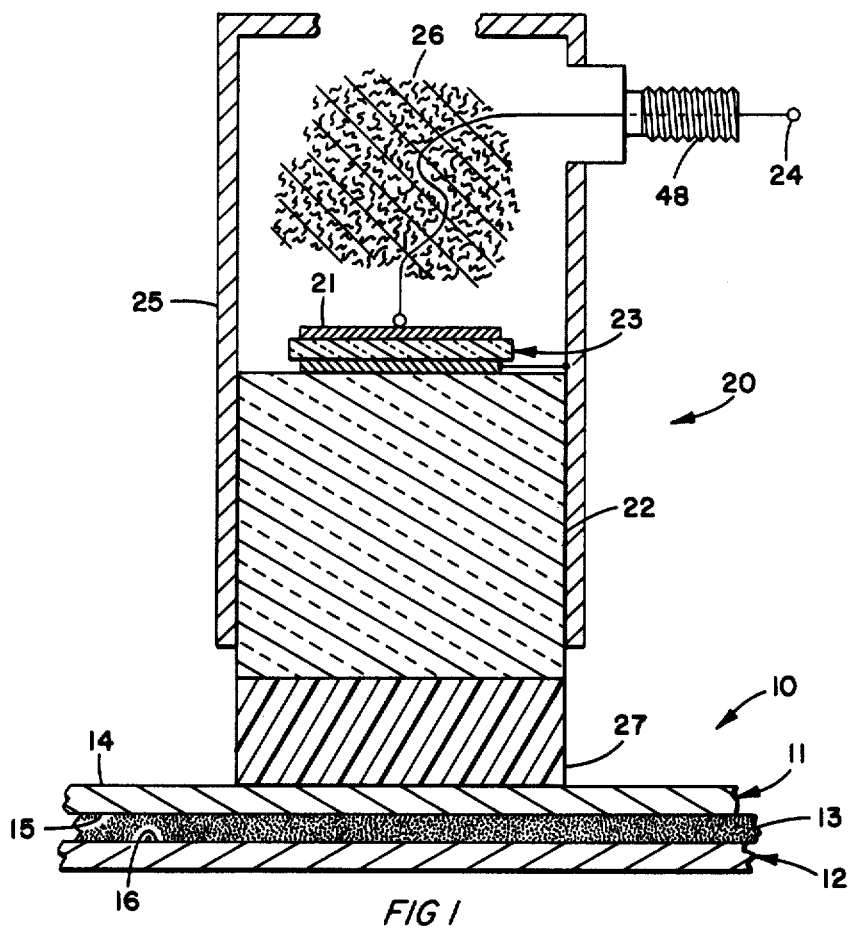
FIG I
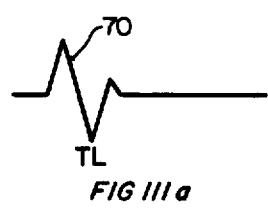
FIG IIIa
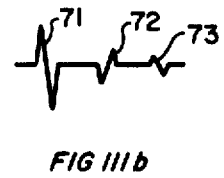
FIG IIIb
FIG IIIc
FIG IIId
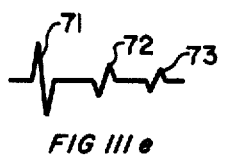
FIG IIIe
FIG IIIf
FIG III

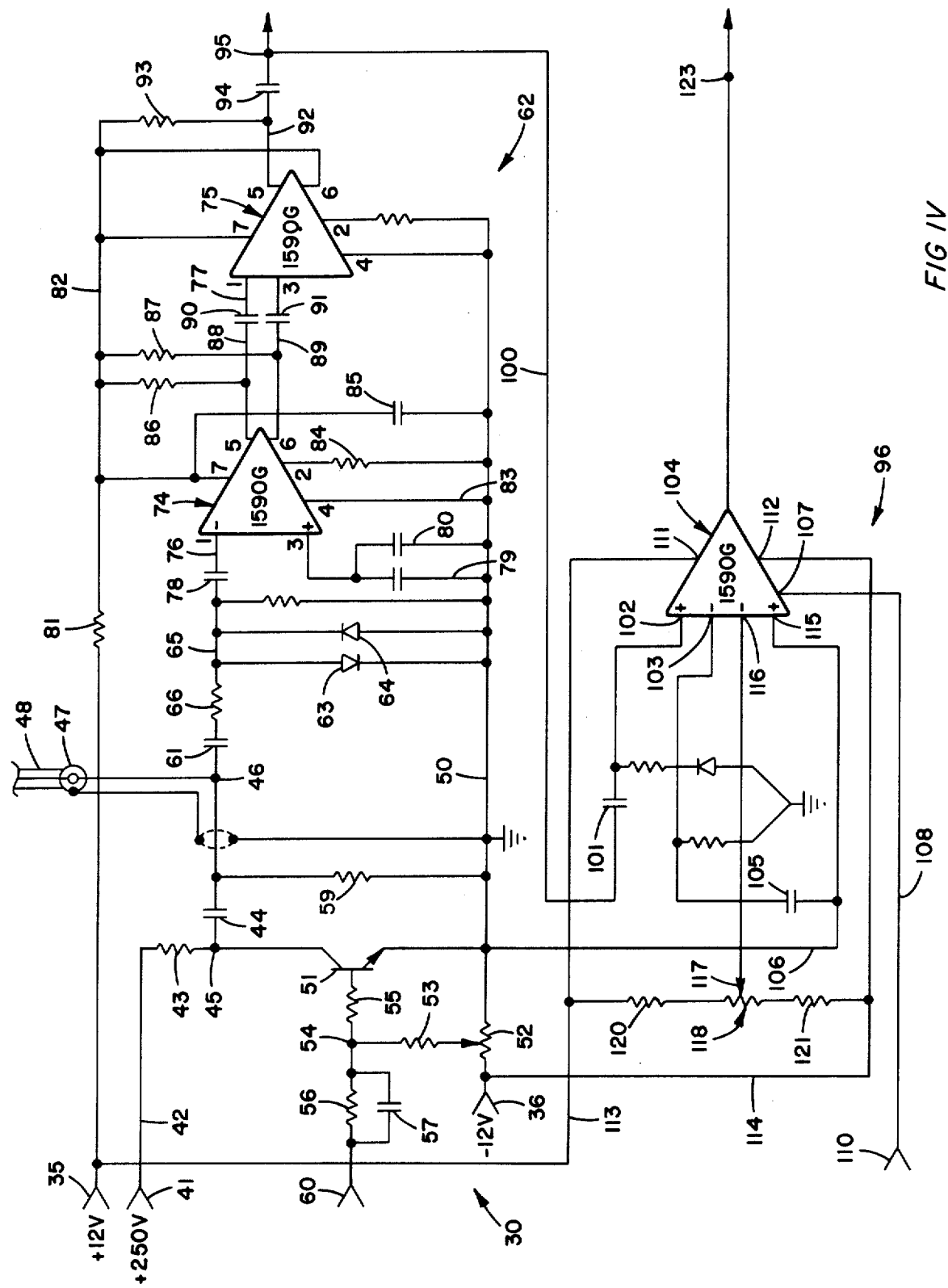
FIG IV

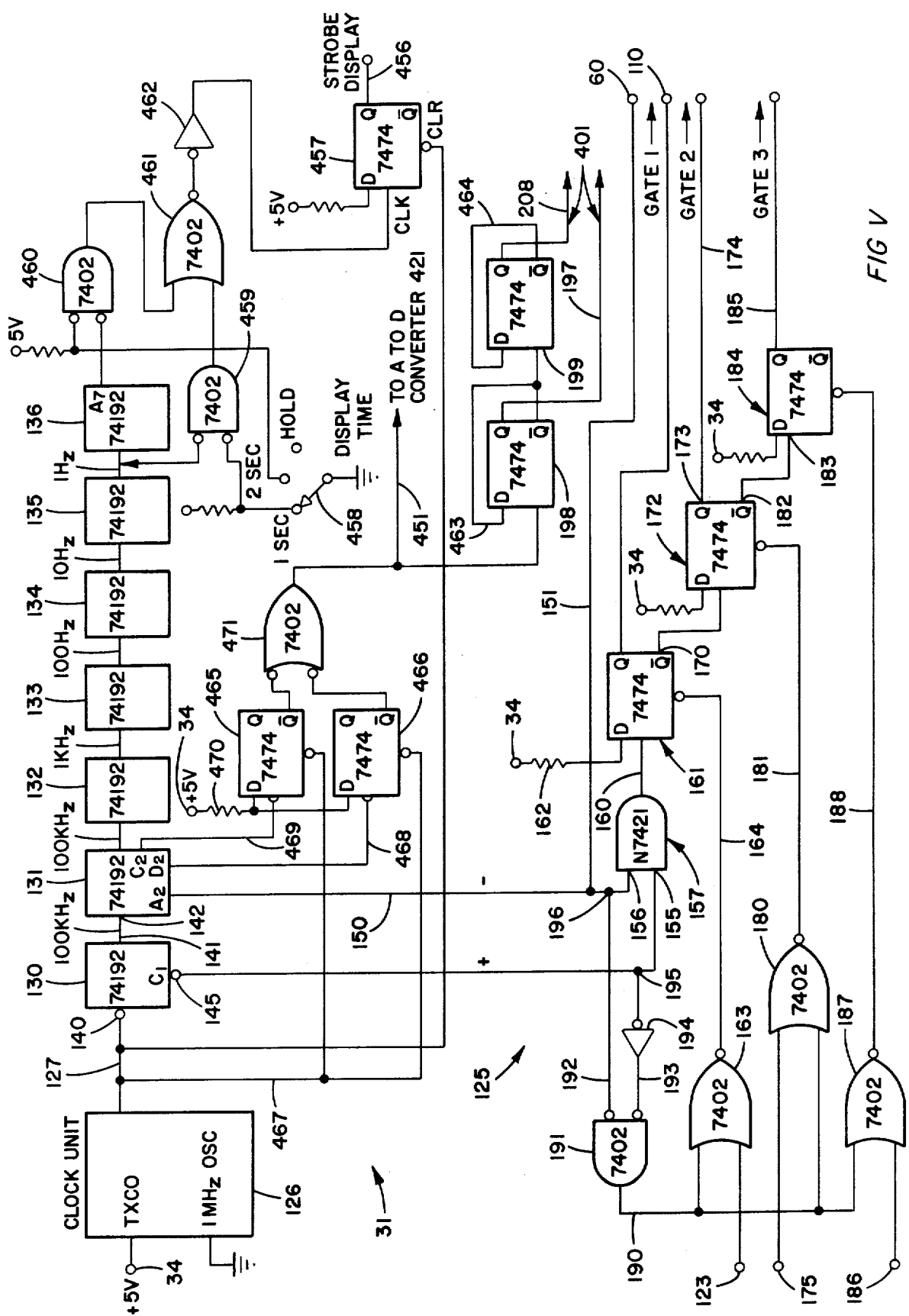

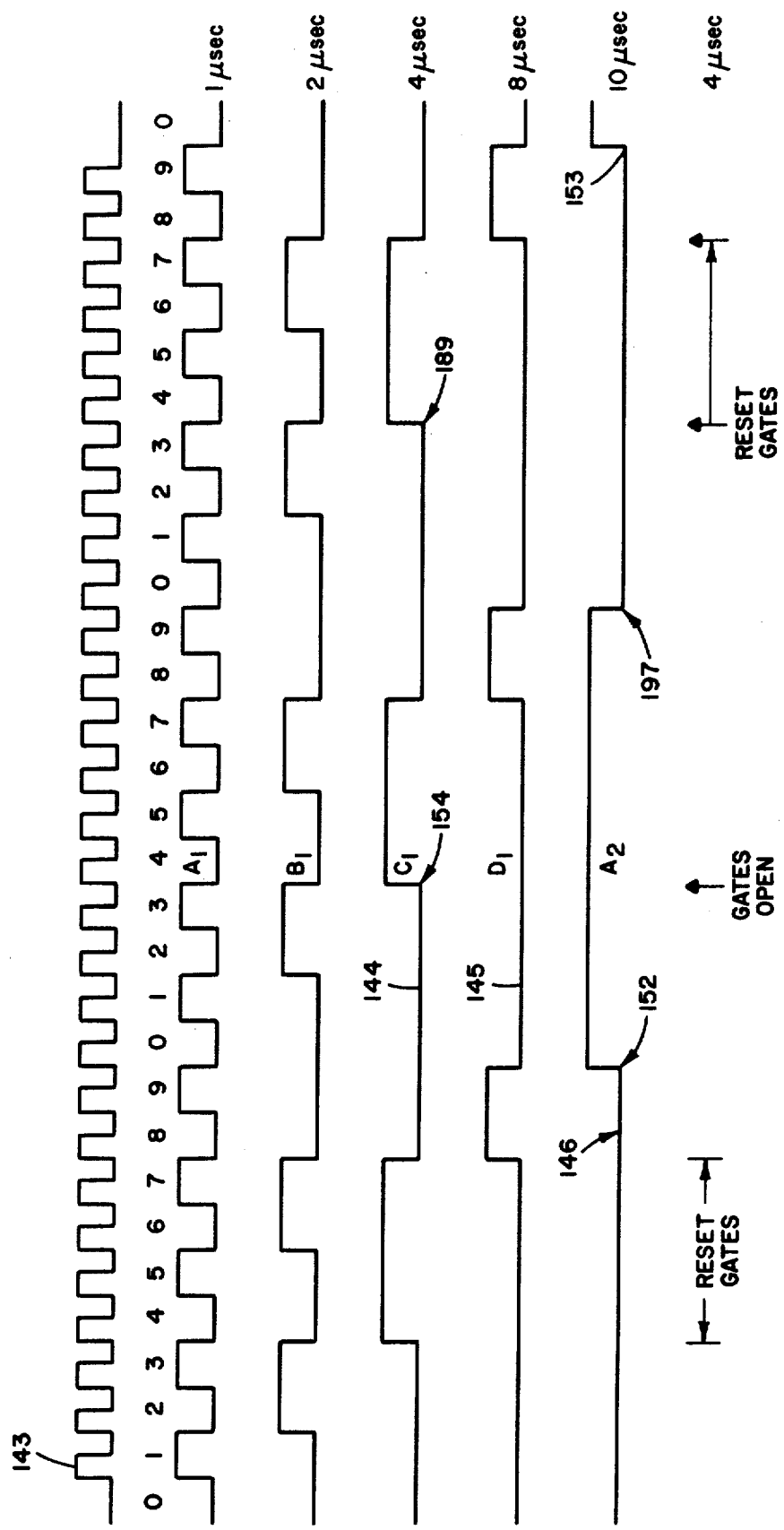
FIG VI

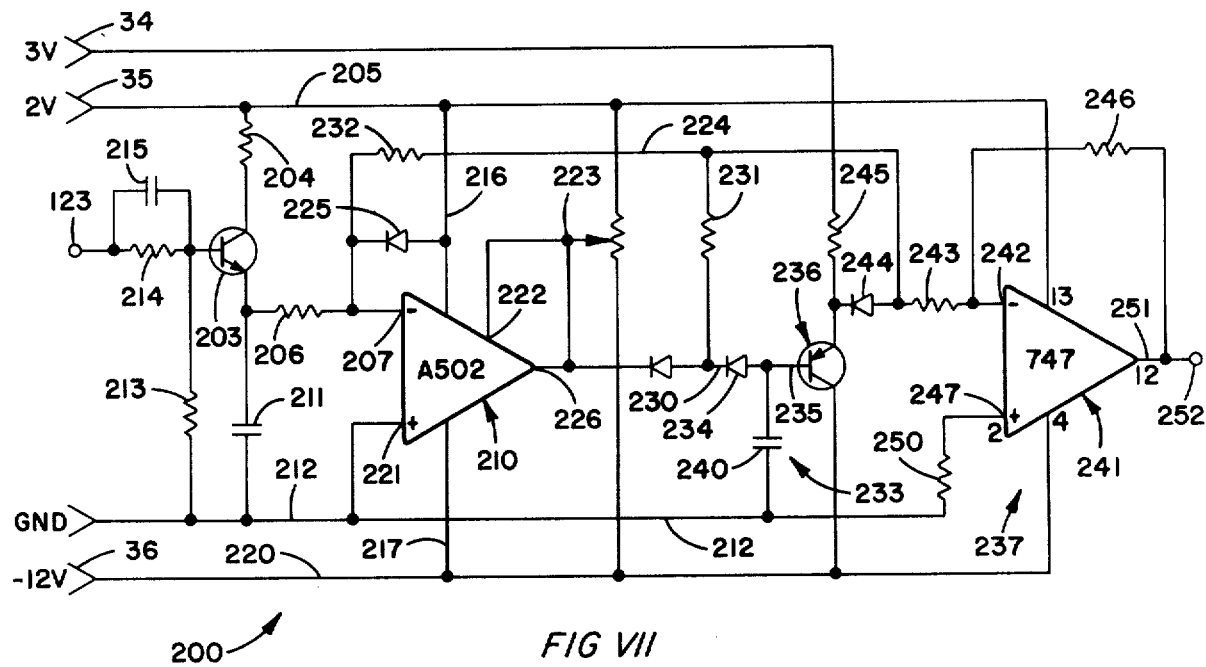
FIG VII
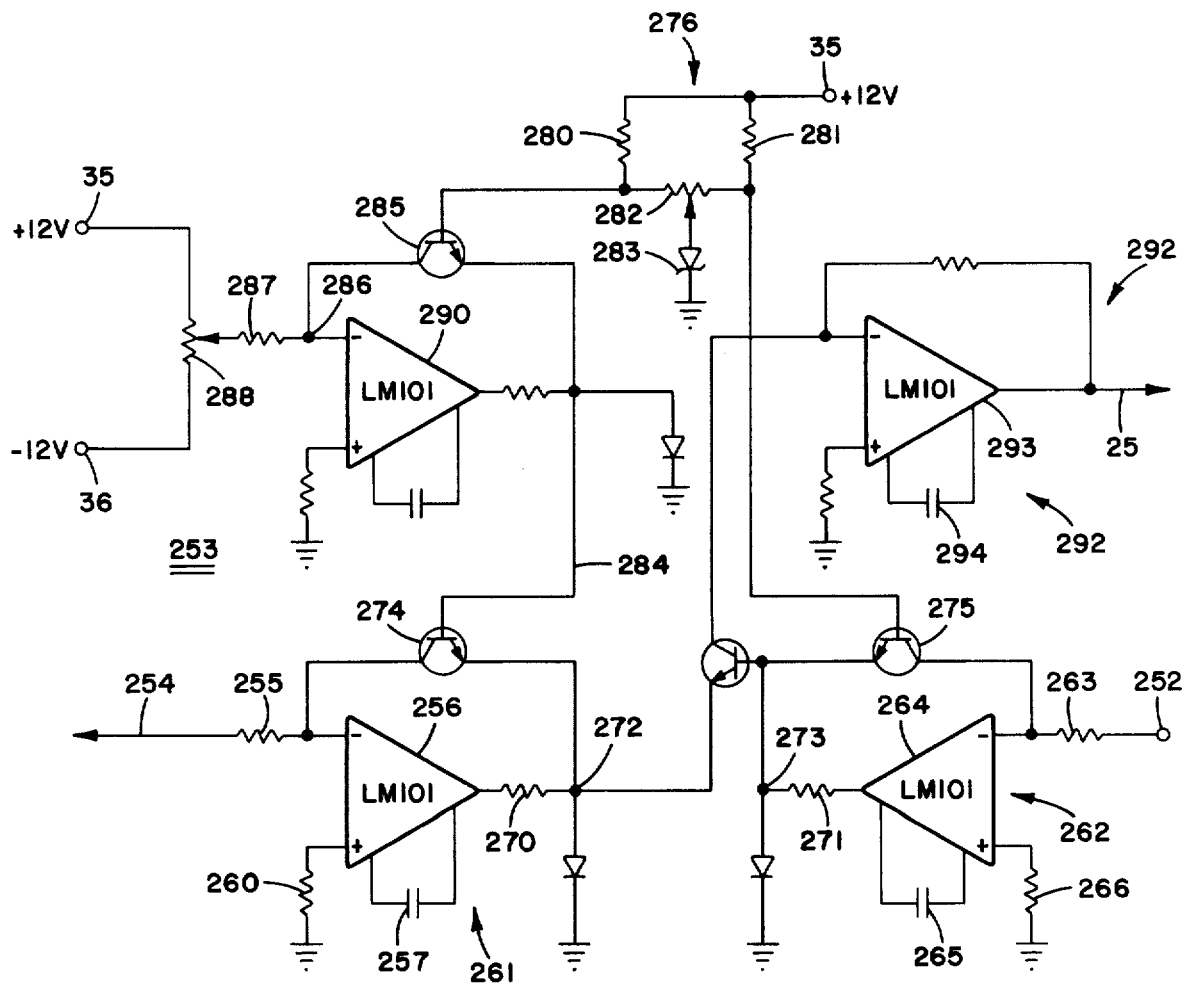
FIG VIII

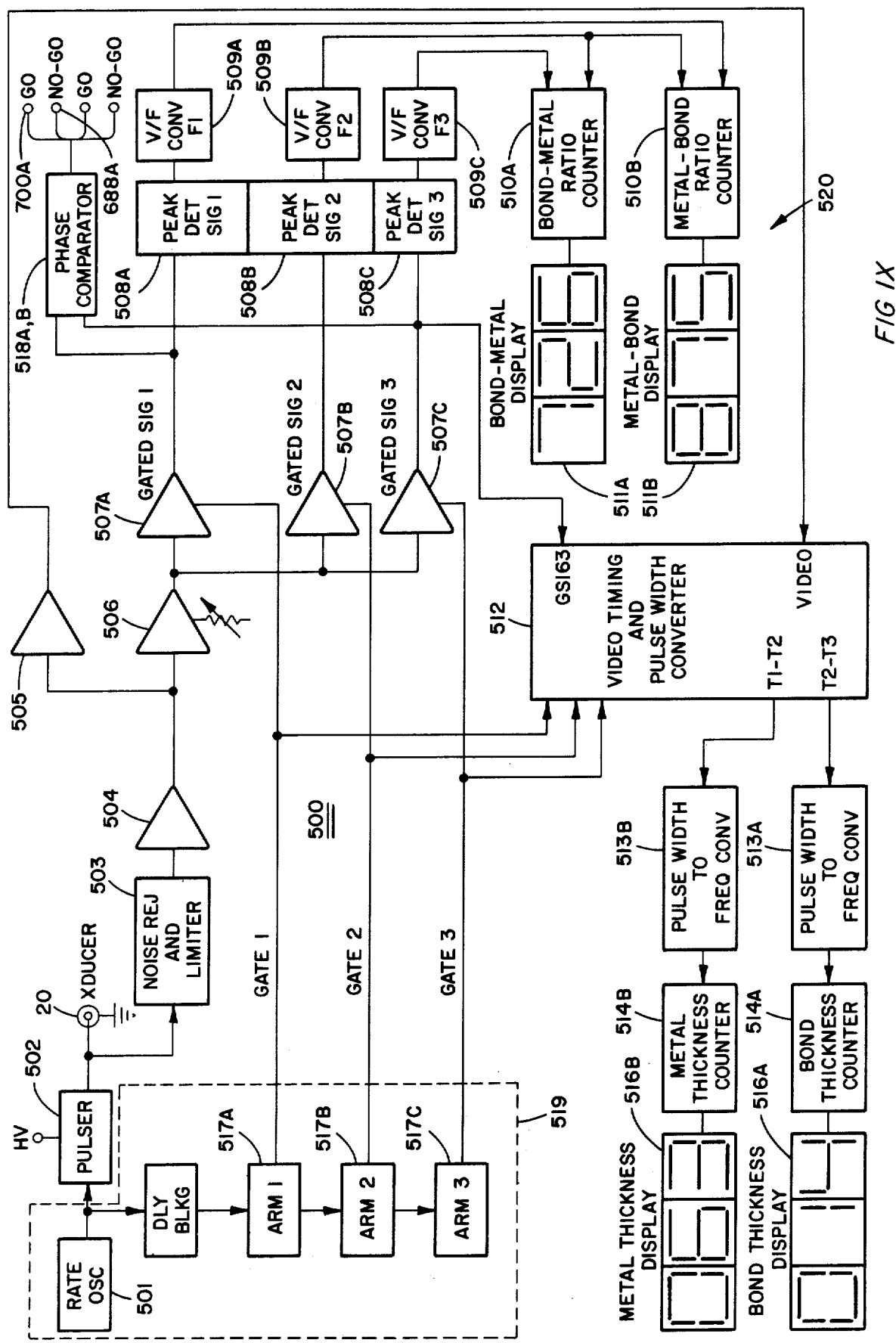
FIG IX

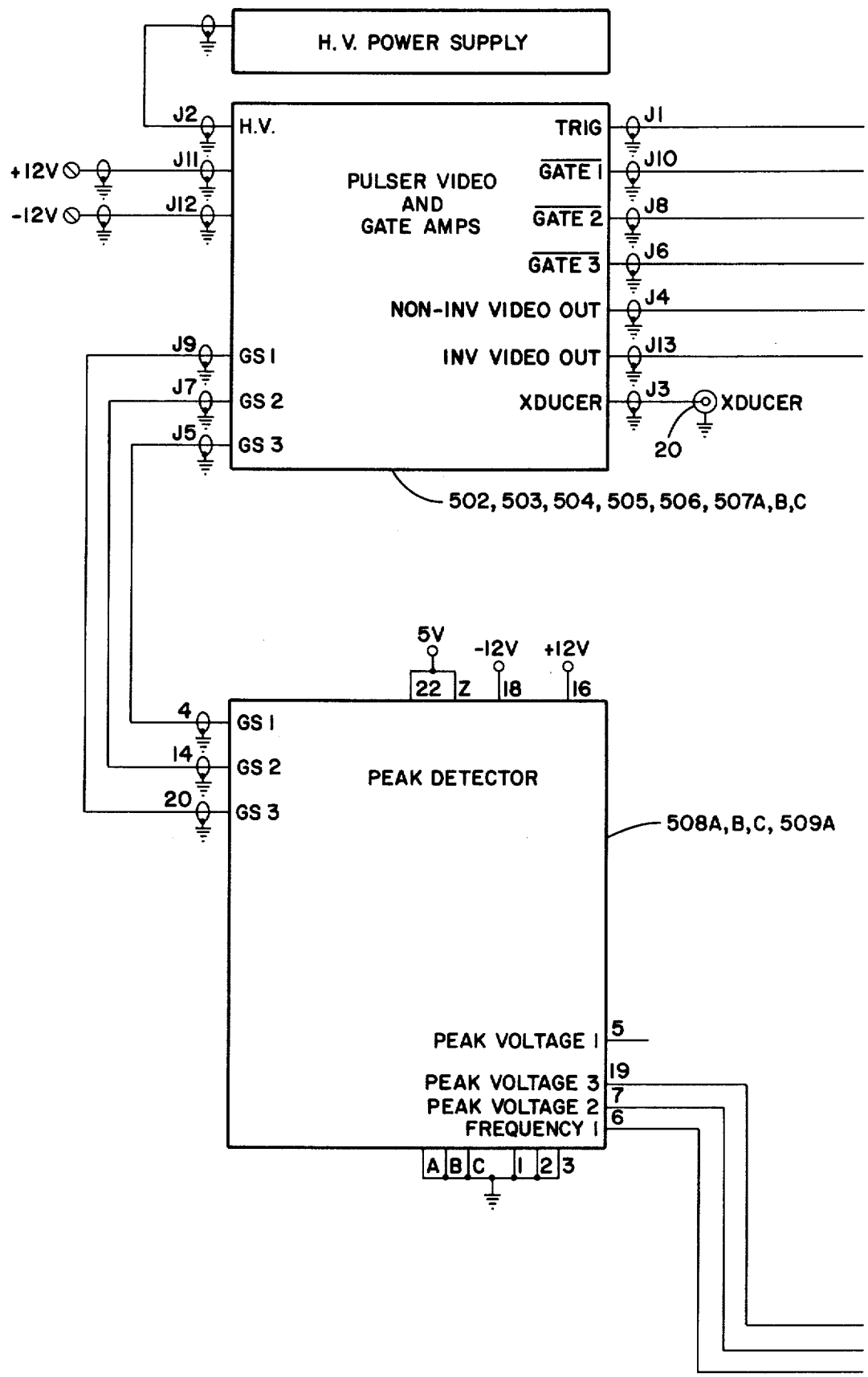
FIG Xa

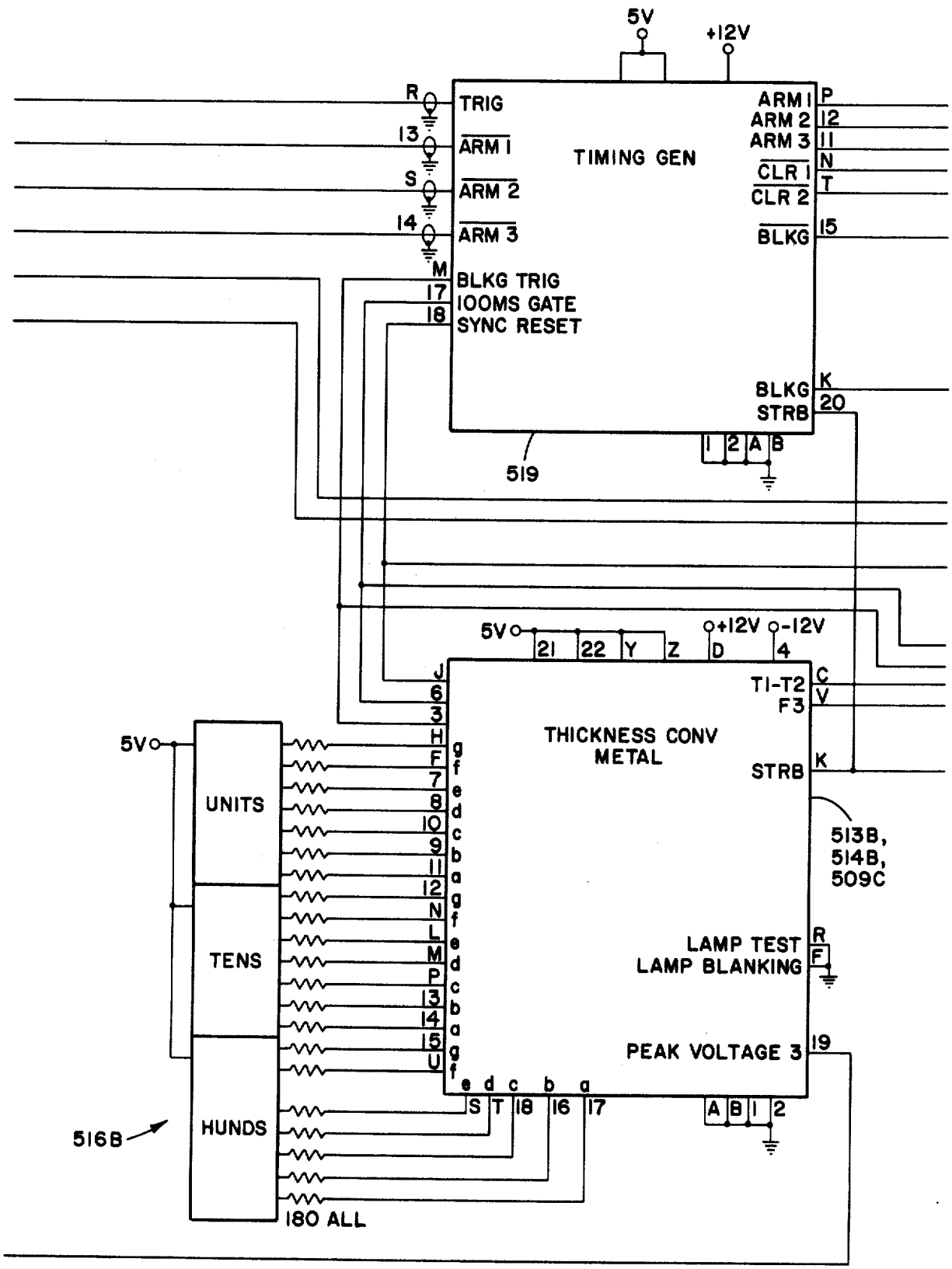
FIG Xb

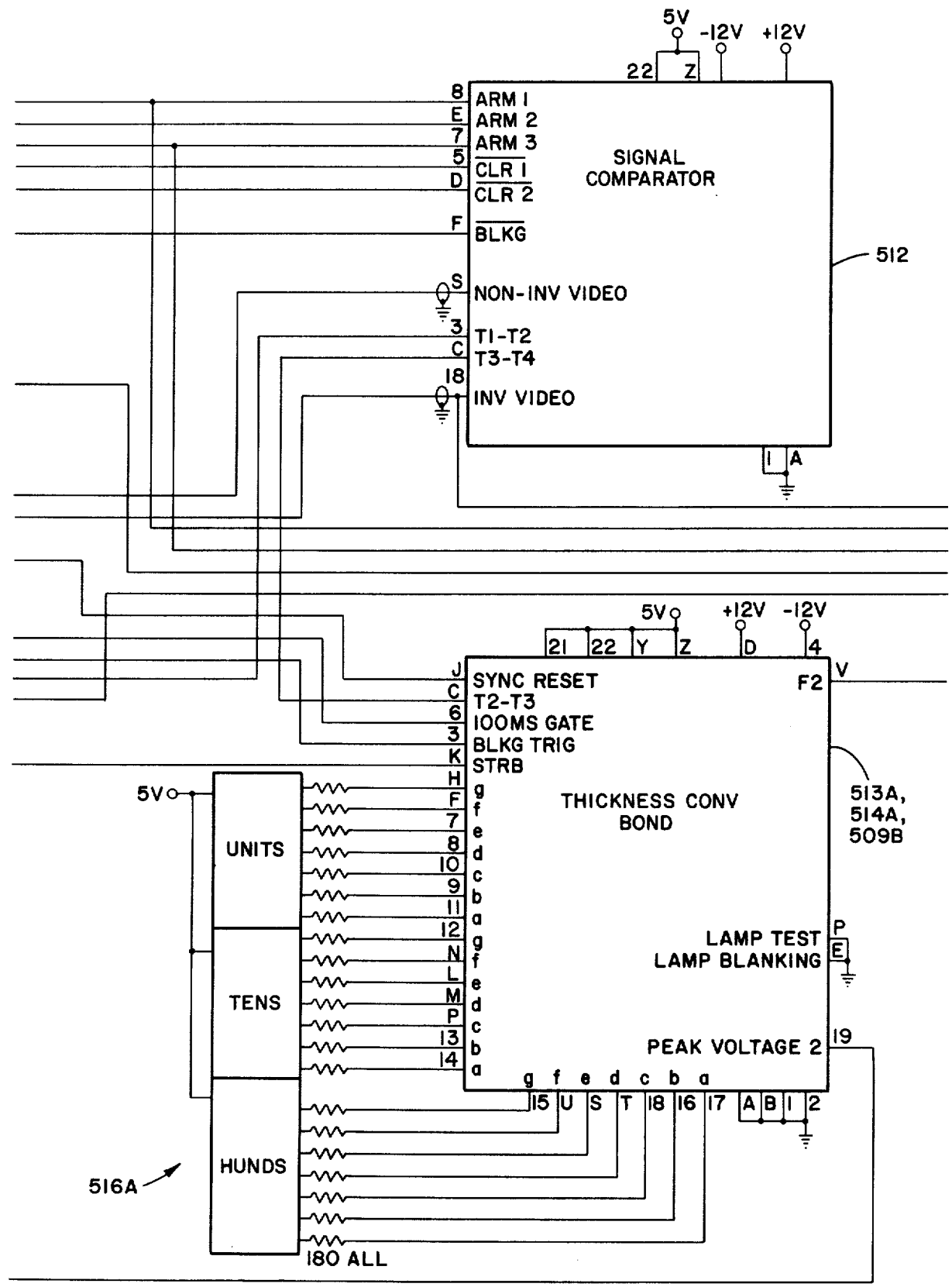
FIG Xc

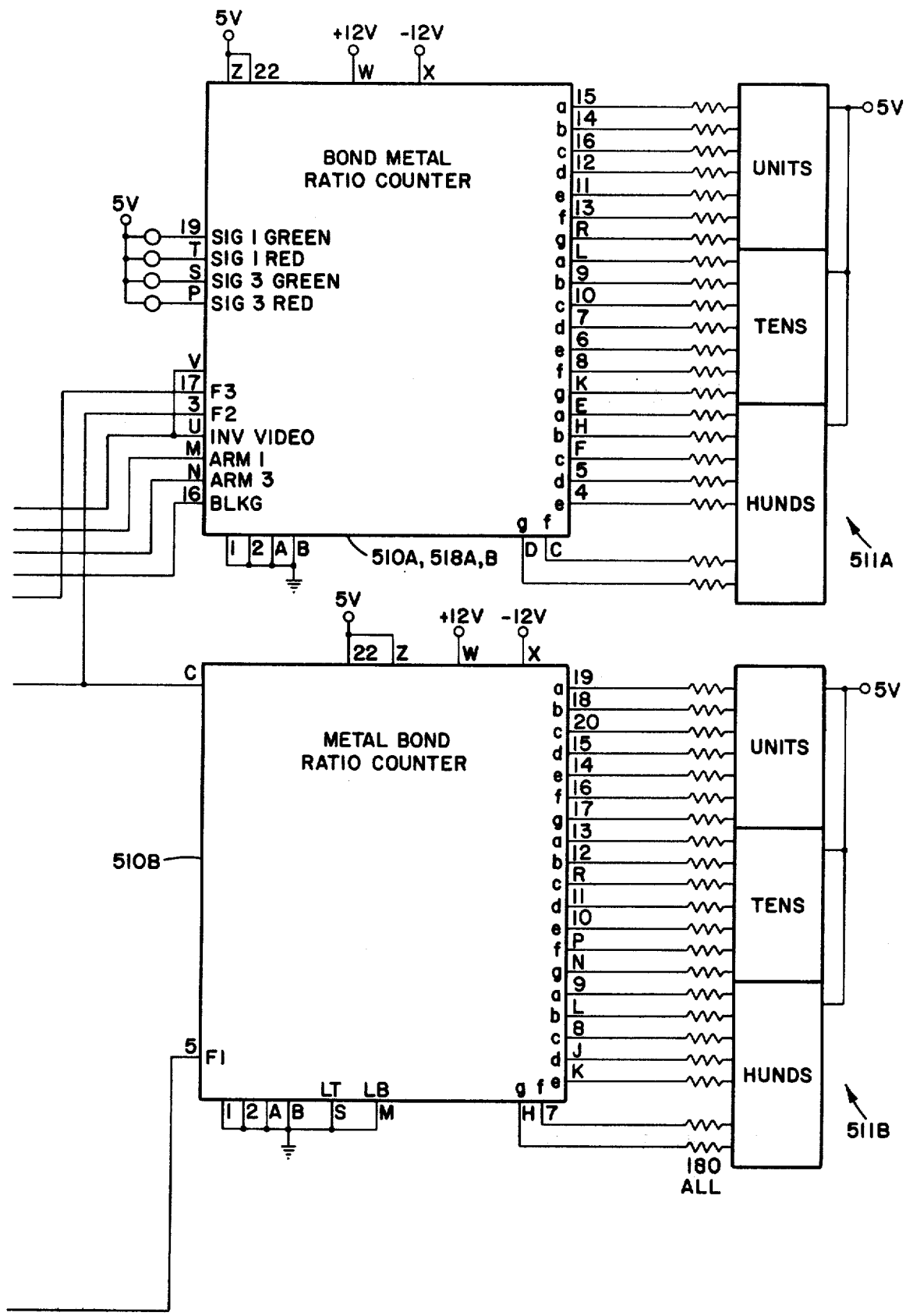
FIG Xd

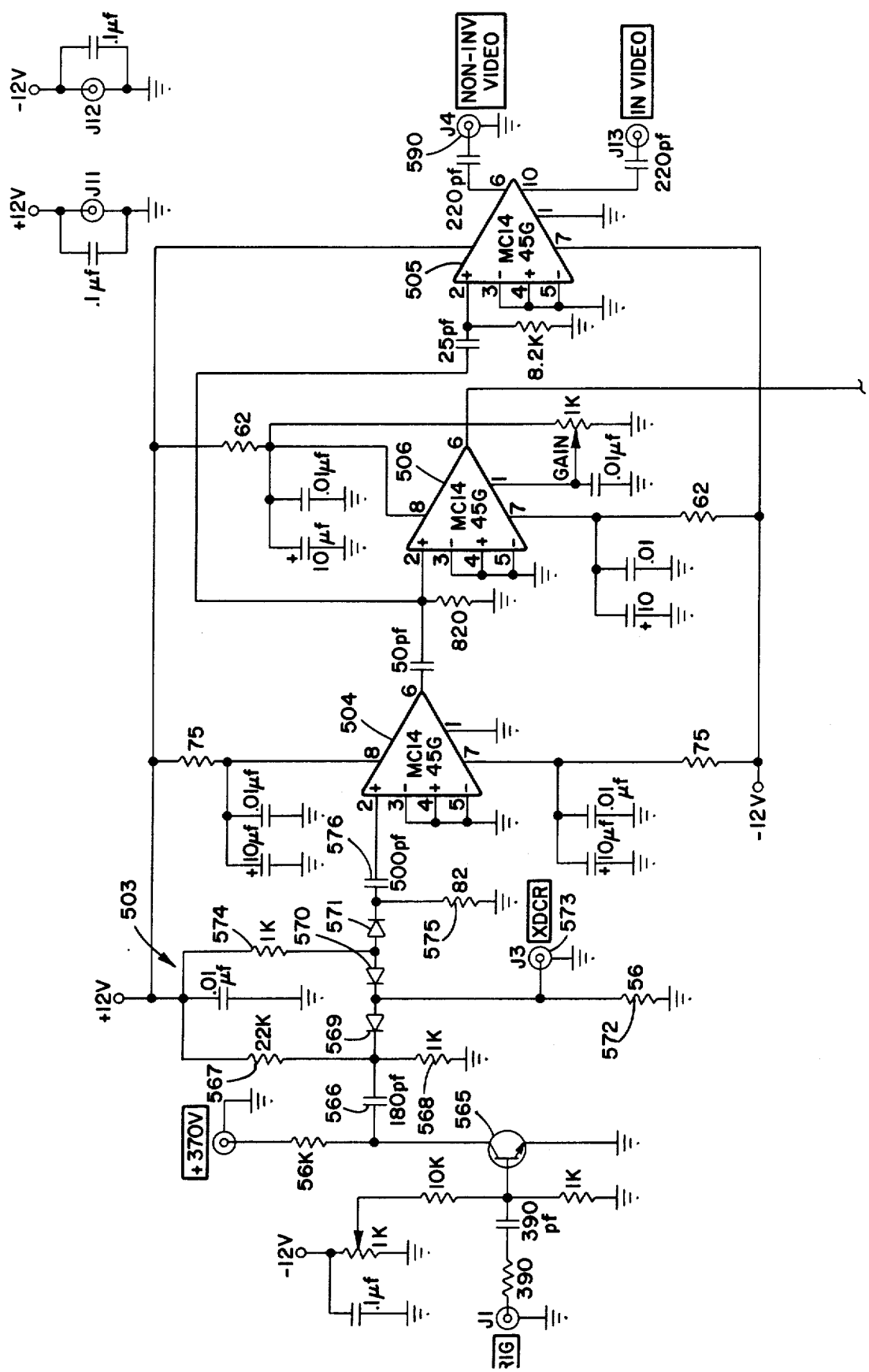
FIG XIa

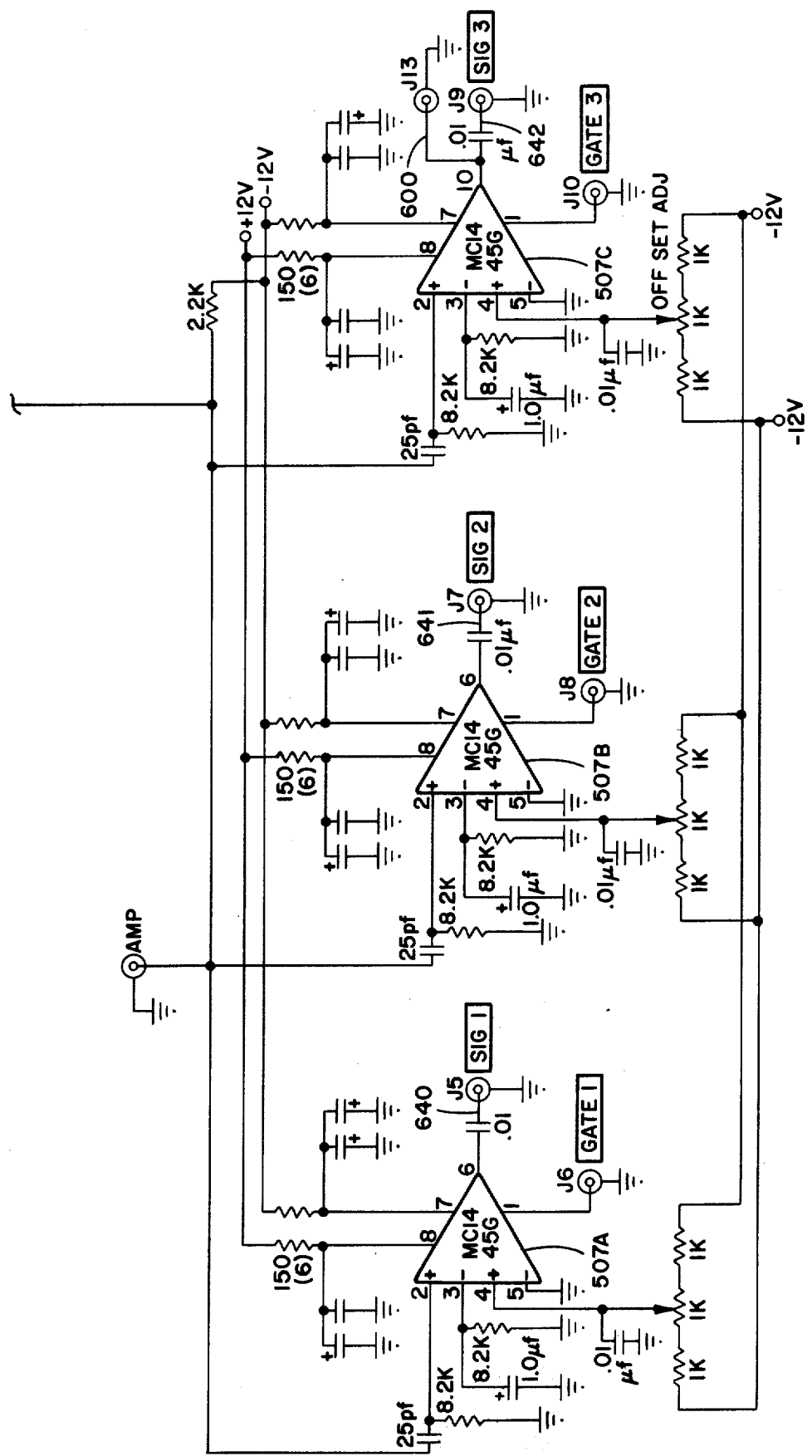
FIG XIb

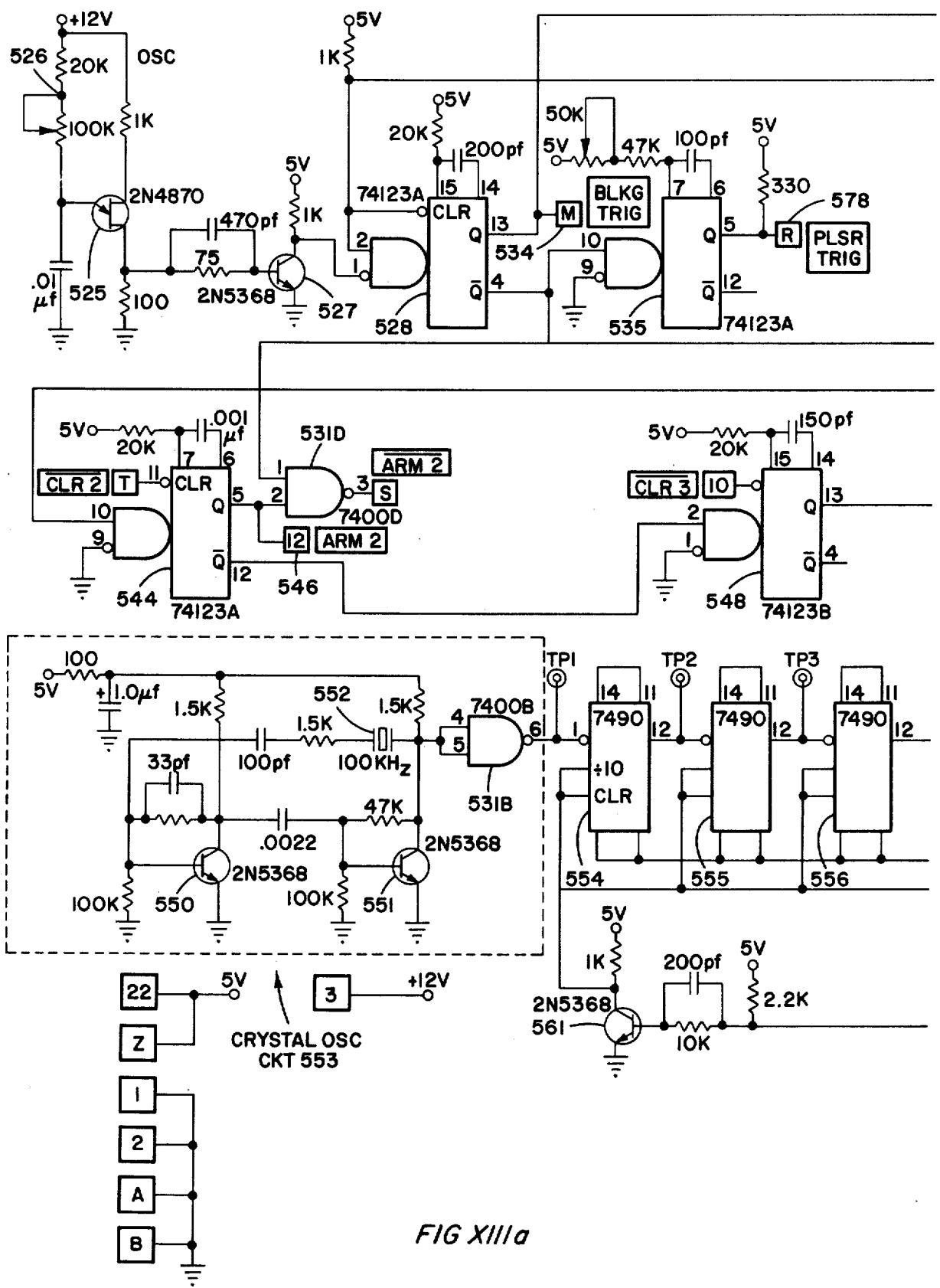
FIG XIIIa

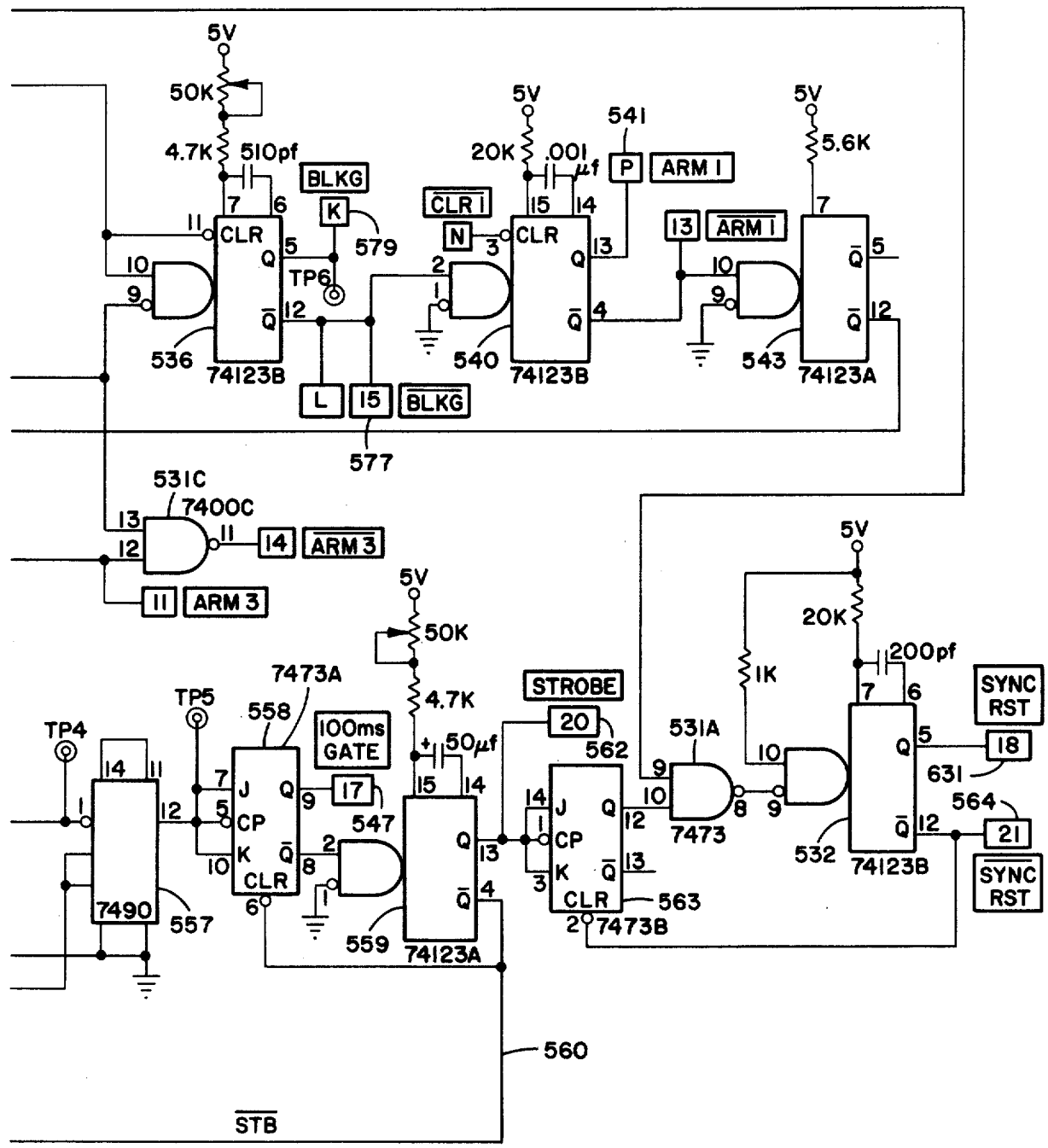
FIG XIIIb

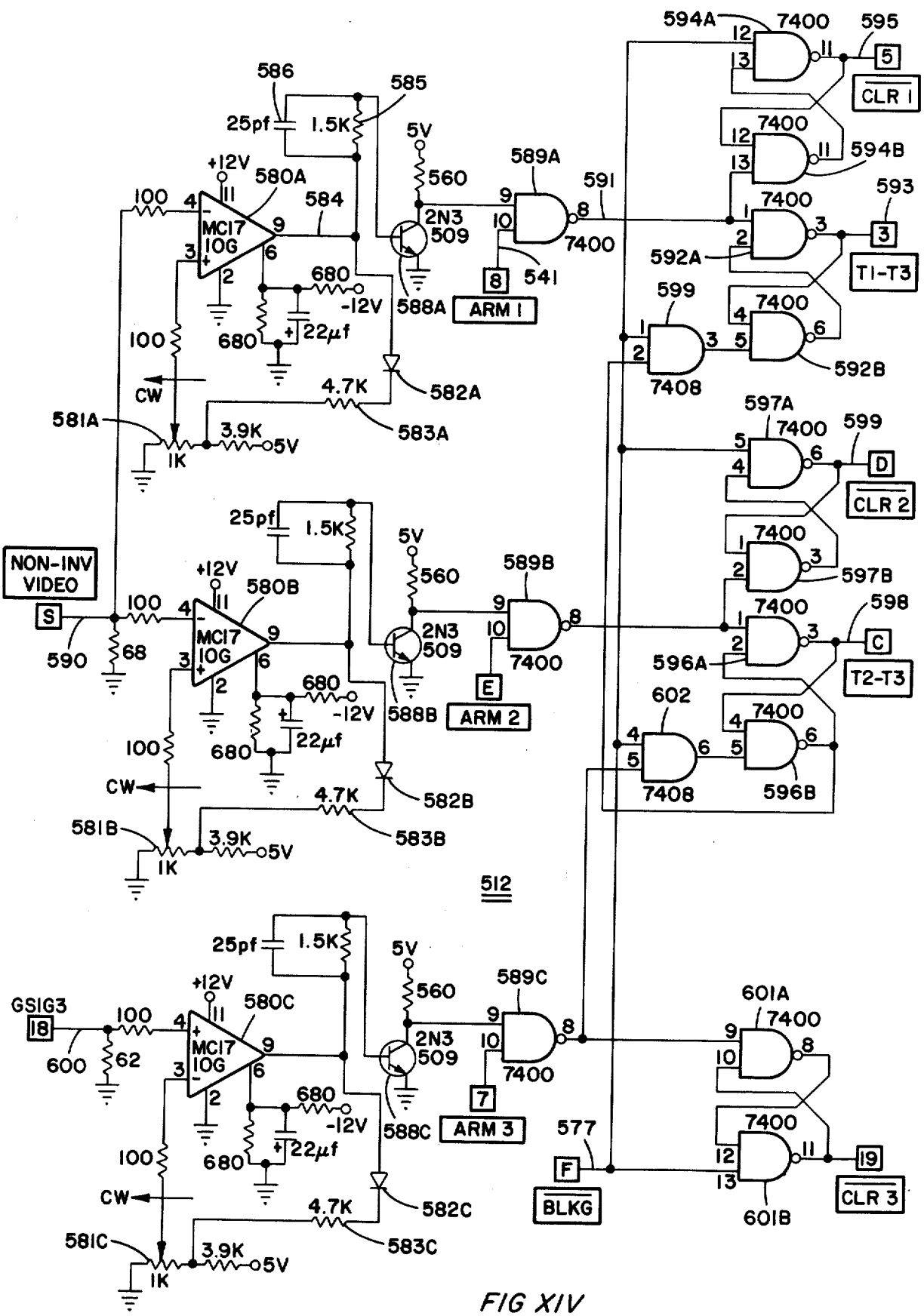
FIG XIV

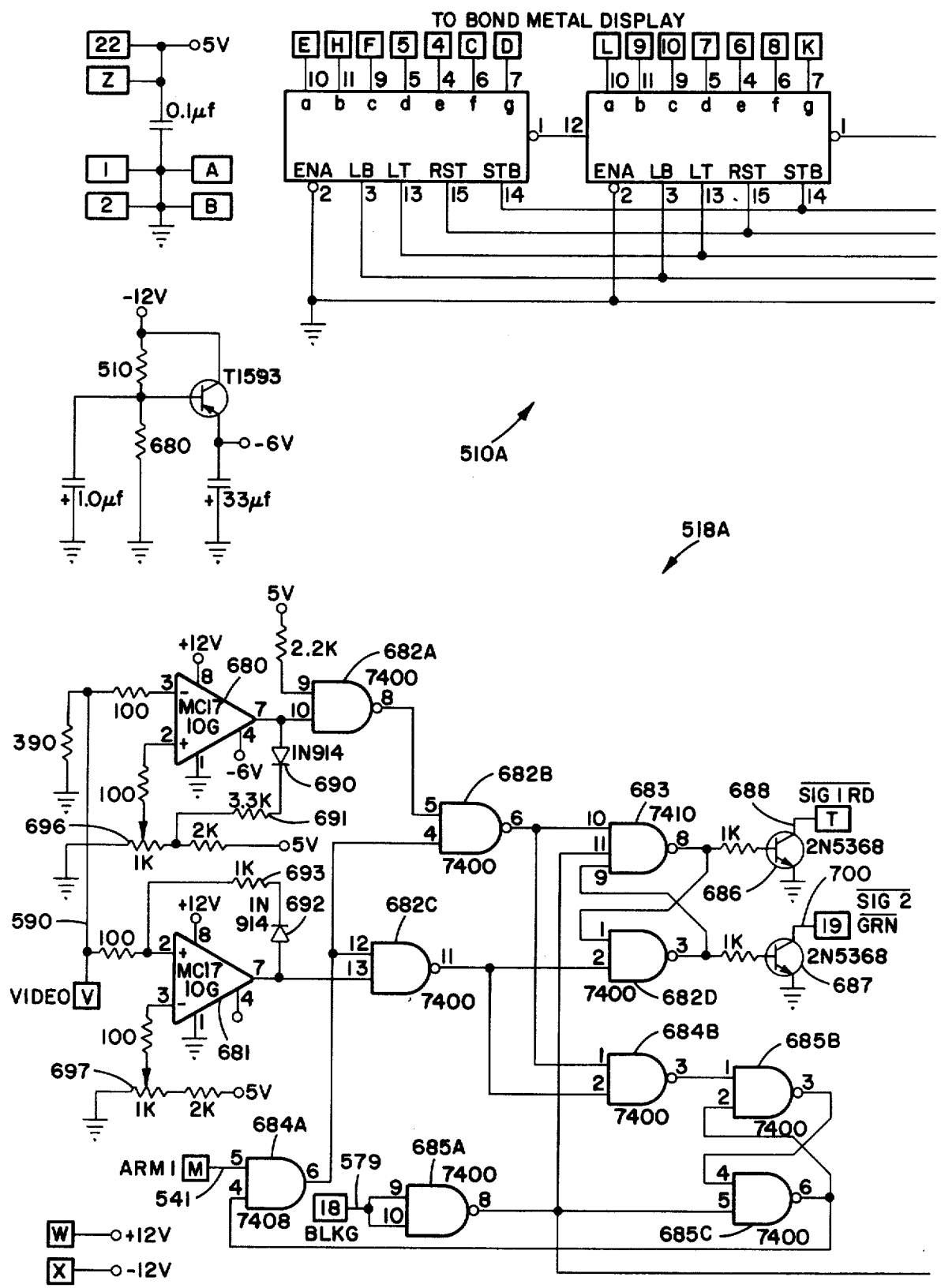
FIG XVa

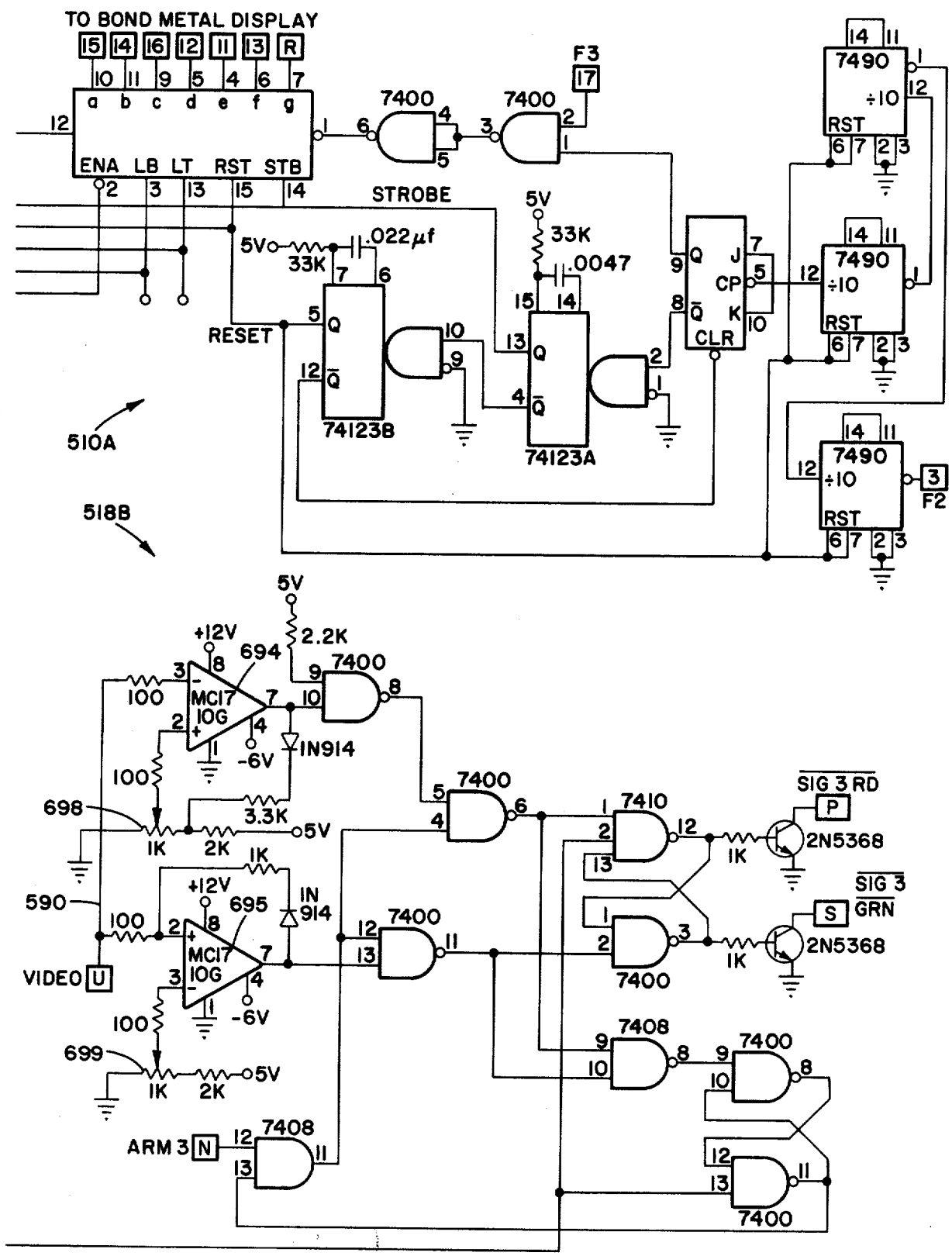
FIG XVb

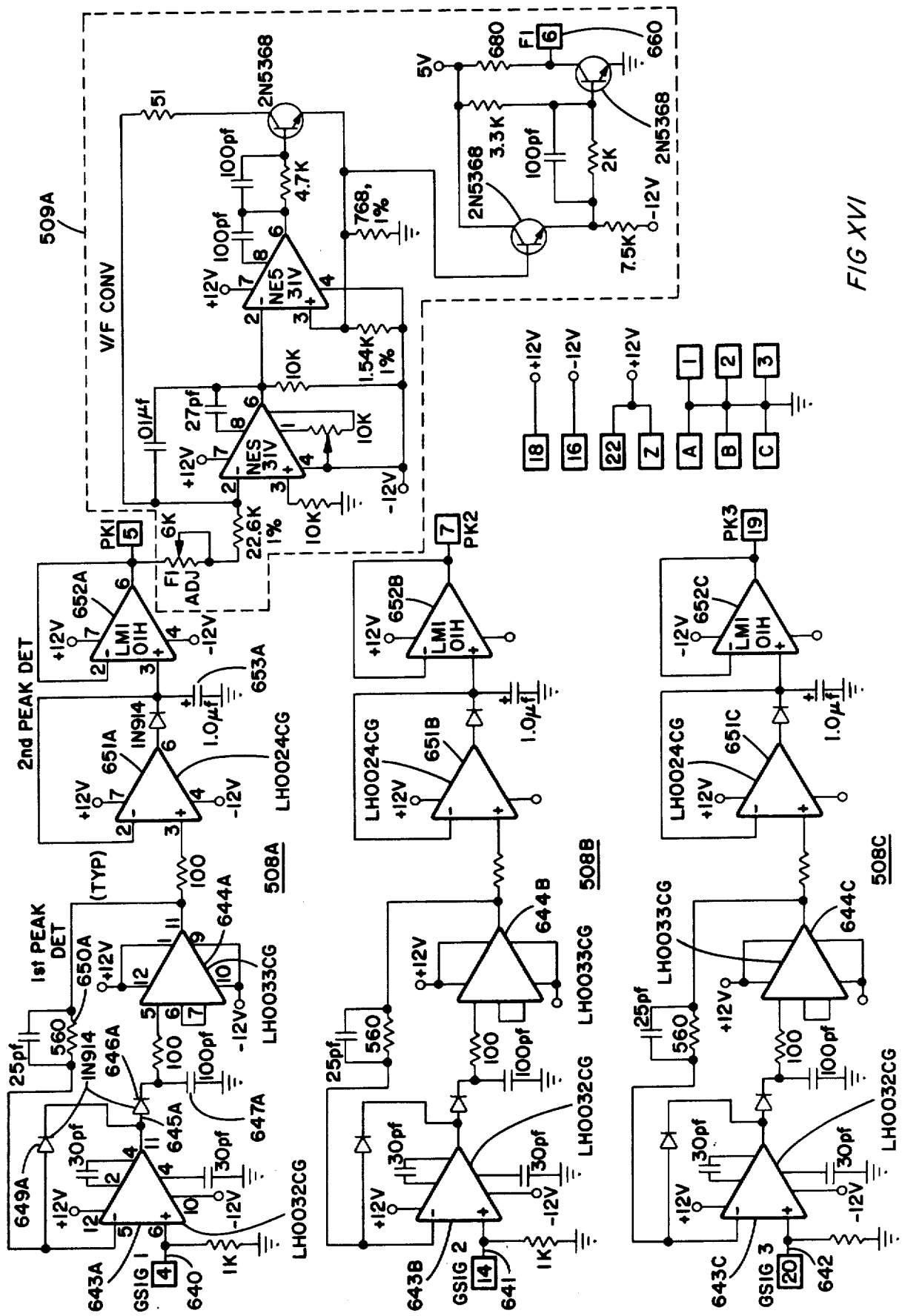
FIG XVI

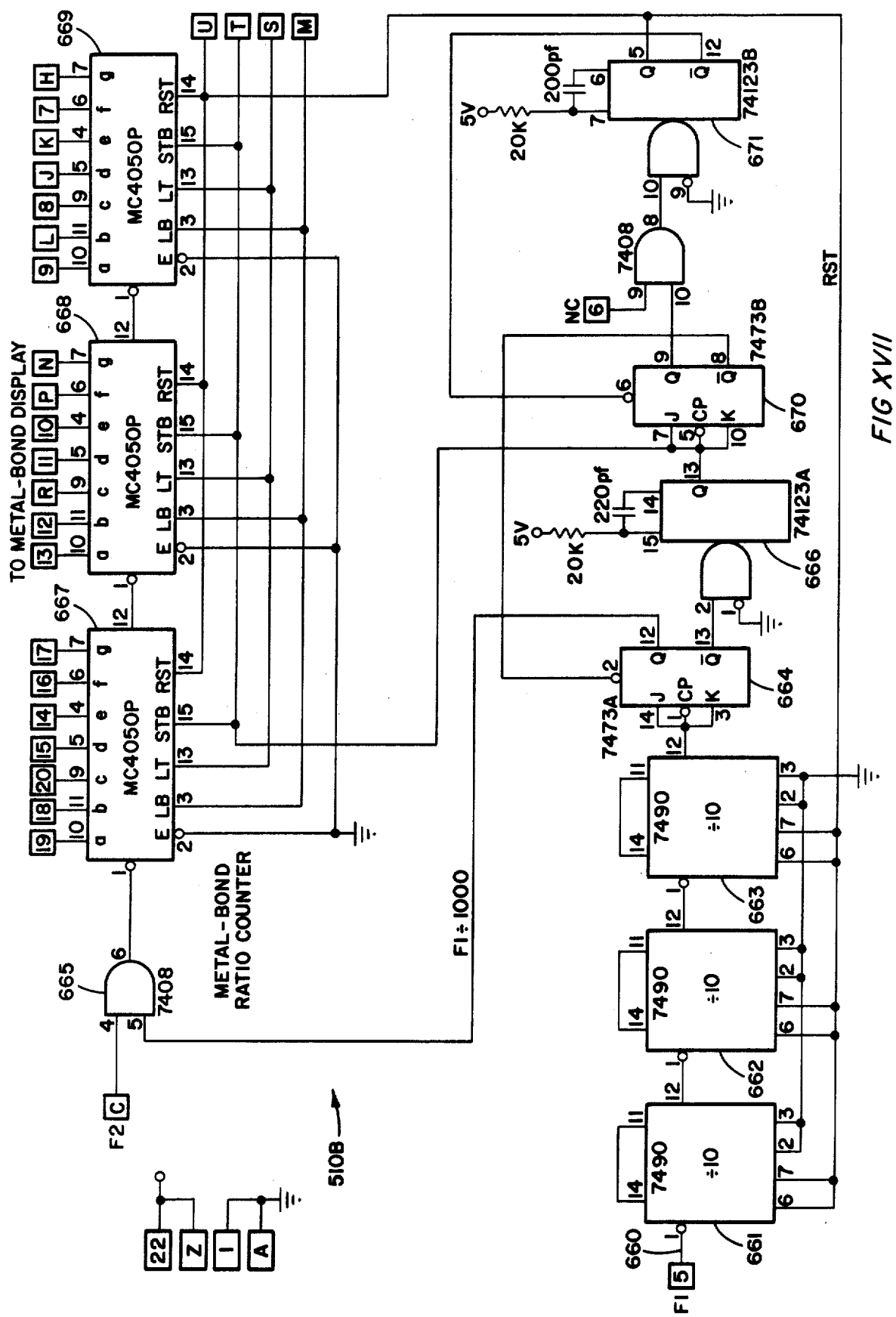
FIG XVII

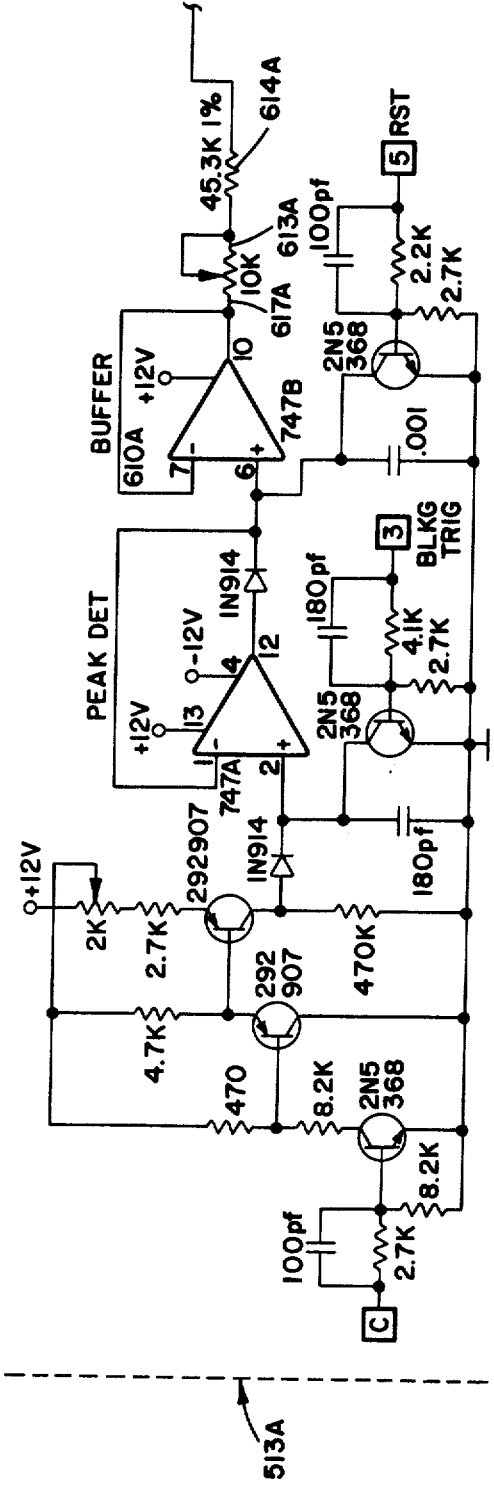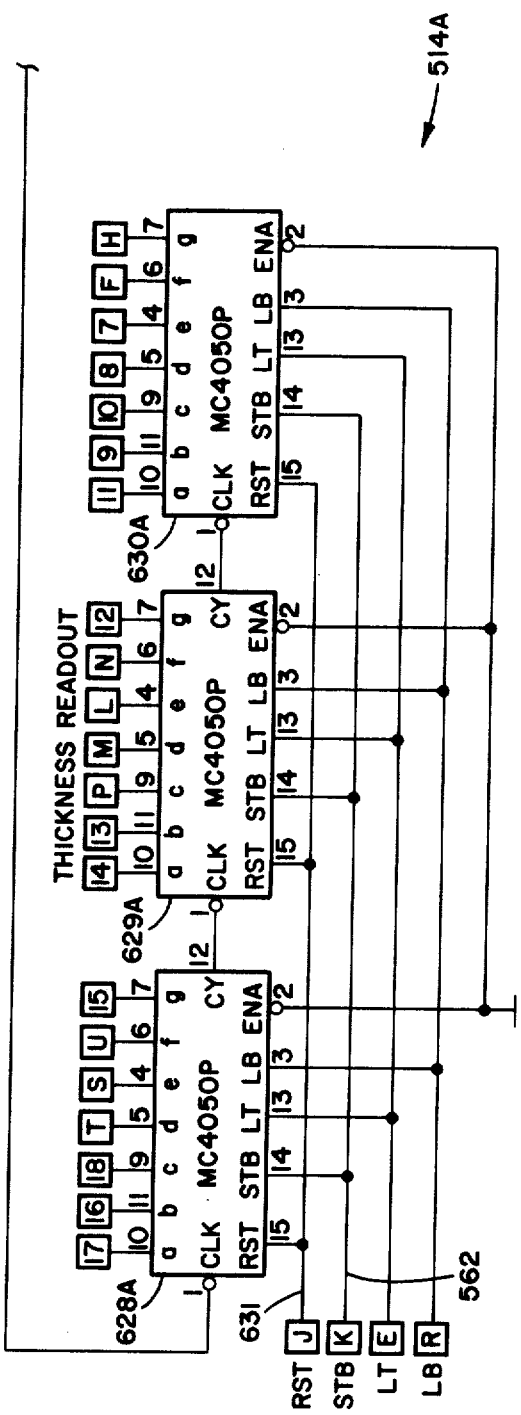
FIG XVIIIa

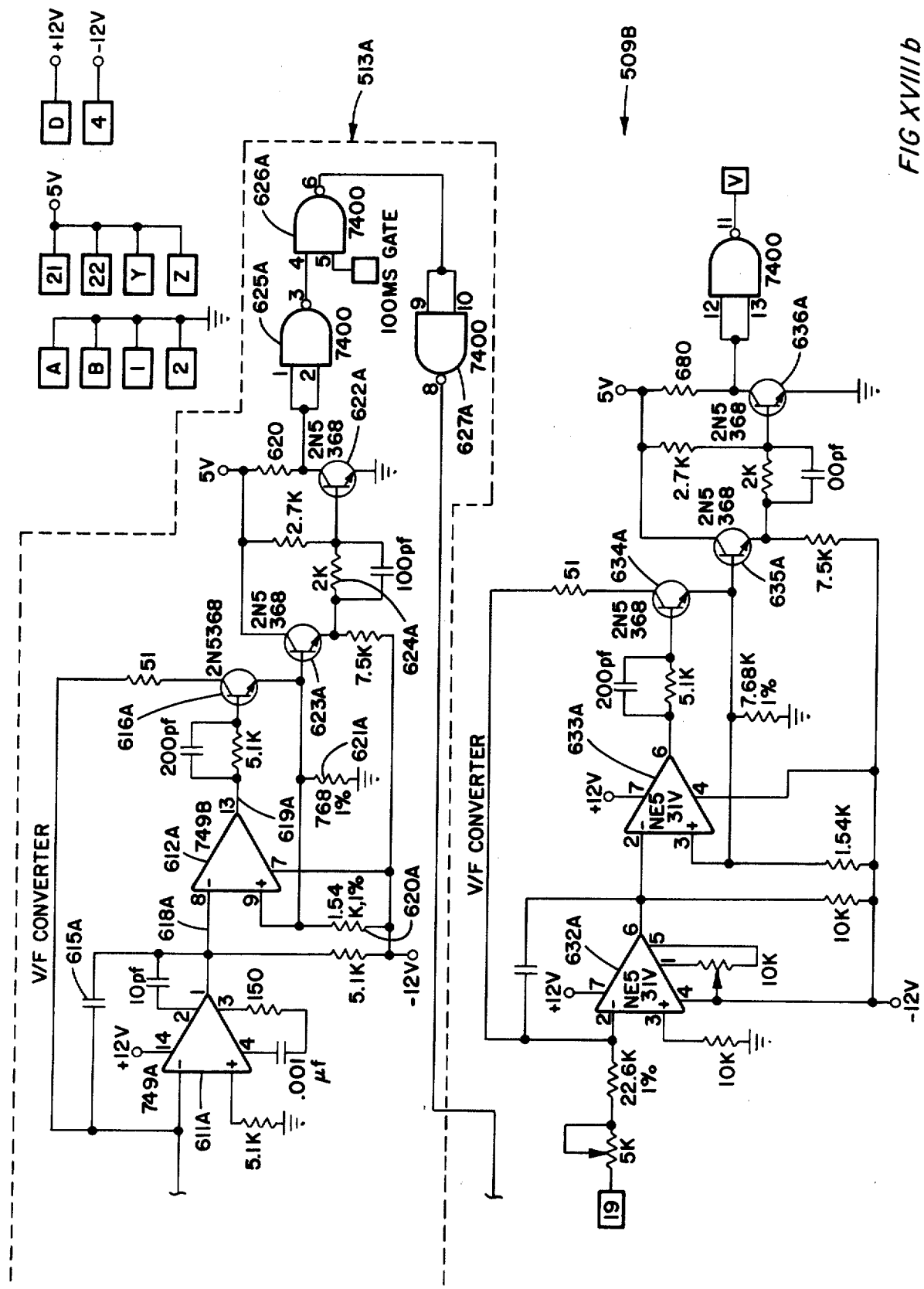
FIG XVIIIb

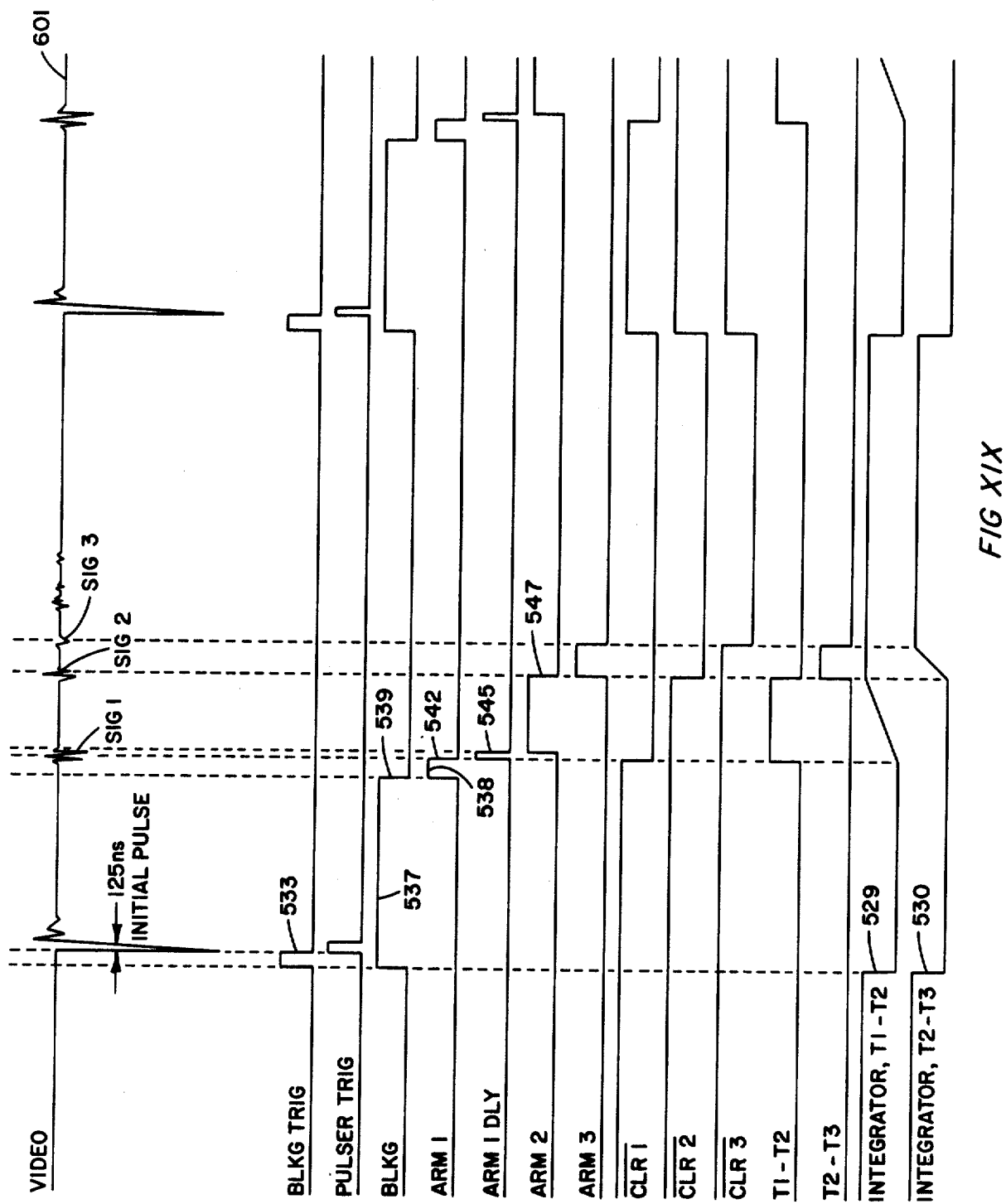
FIG XIX

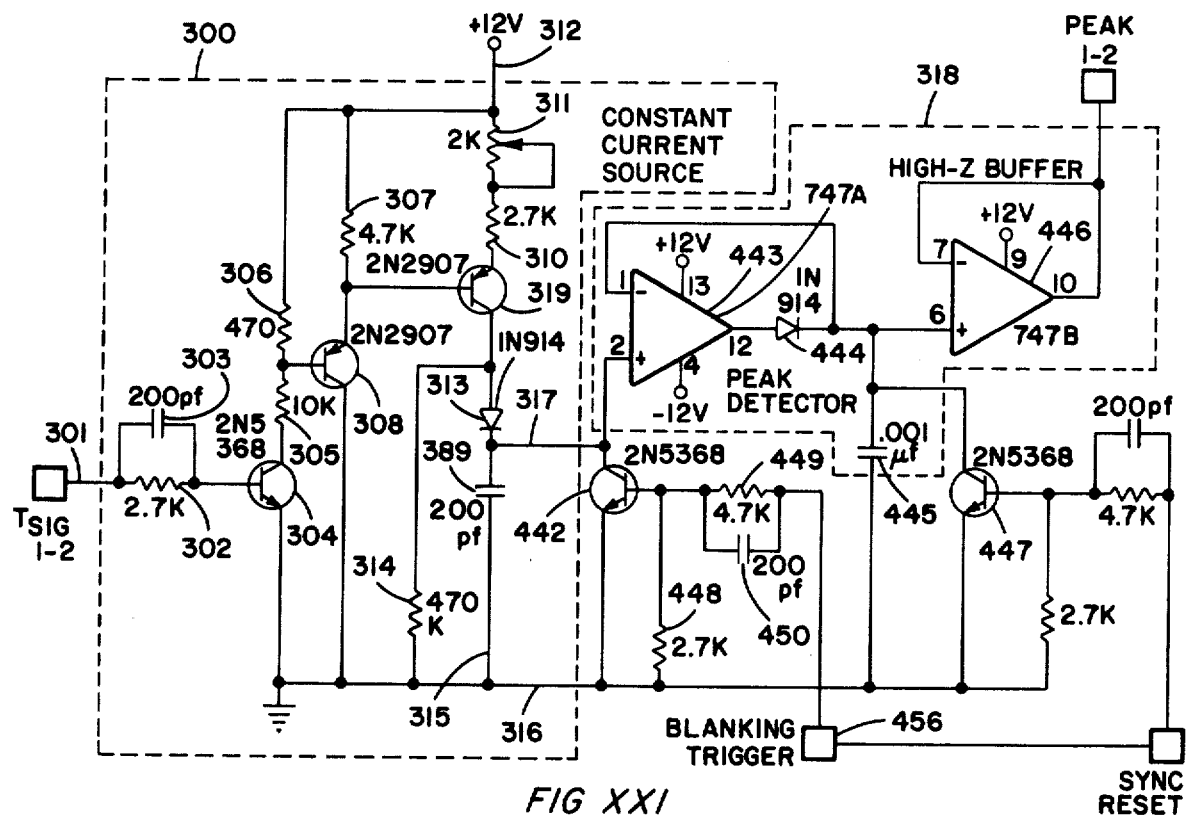
FIG XXI
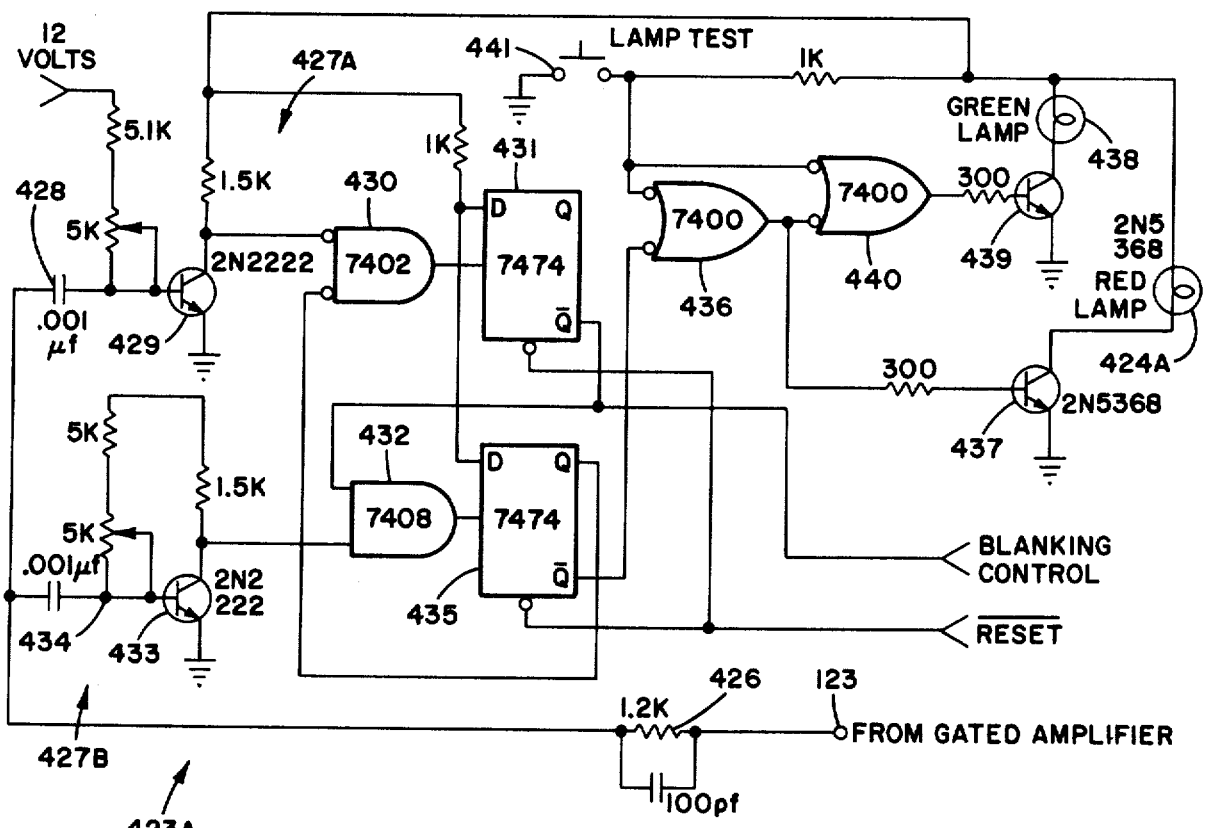
FIG XXII

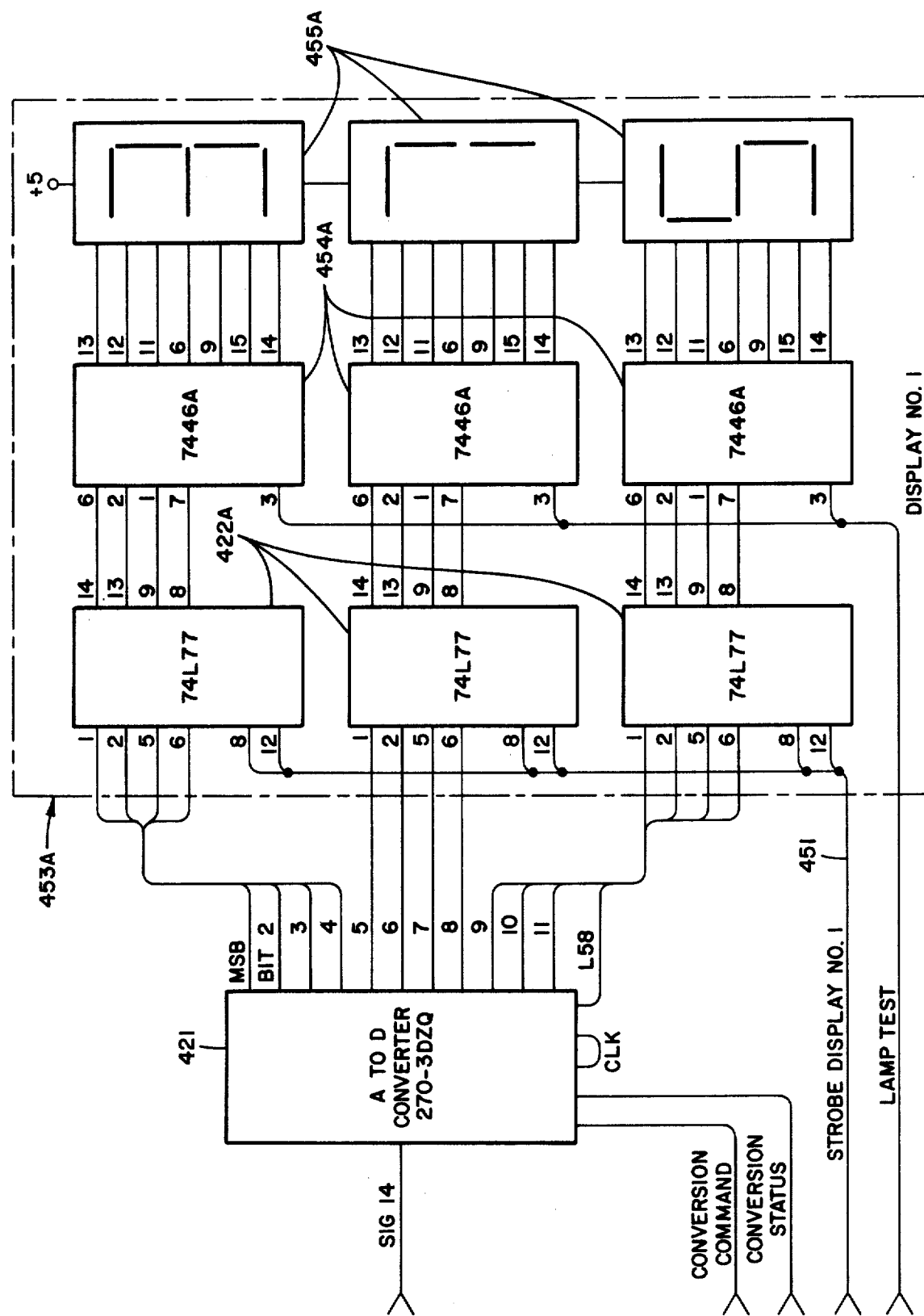
FIG XXIII

APPARATUS FOR EVALUATING A BOND

This invention relates to testing instruments and, more particularly, to ultrasonic testing instruments for evaluating bonded structures.

Processes for the bonding together of structural members have been greatly refined in recent years, and such bonding processes are increasingly employed in place of conventional fastening methods such as those employing bolts, rivets, welded joints or the like. Advantages inherent in the use of adhesive bonding processes include weight reduction, cost benefits, increased speed of application, and adaptability for efficient use in automated or mechanized production processes. While it has been recognized that modern adhesives are potentially of sufficient strength for use in fastening together the structural components of such products as automobiles, buildings, and even aircraft, their widespread use in such high stress applications has been somewhat limited. One major reason for this has been the difficulty of obtaining completely reliable test data concerning the consistency and strength of bonded joints without destroying the bonded structure. Thus, it is sometimes necessary to test a high percentage of the bonded joints in composite structures which in use may be subject to stress, or which are to be used in critical applications such as aircraft structural components or the like; and it has thus far been impossible to predict with consistent accuracy the strength and durability of such bonded joints by conventional, nondestructive testing methods.

In the past, various nondestructive bond testing procedures have been proposed, some of which employ the use of ultrasonic energy directed into the bonded structure as in the present invention. These procedures, however, have largely employed ultrasonic techniques fo measuring changes in the mechanical impedance of the test structure, which may be caused by voids or irregularities in an intermediate adhesive layer. While voids in a composite construction do alter the impedance of the construction to ultrasonic energy, the impedance may also be affected by other variations among test structures in the properties or dimensions of the composite structures, which variations do not adversely affect the bond strength. Moreover, existing testing apparatus are not capable of indicating the precise nature of a bond fault. Assume for example that a bonded, composite workpiece consists of a first structure bonded to a second structure by an intermediate layer of adhesive. A bond fault or potential bond fault in such a workpiece may involve poor adhesion between the adhesive layer and the first structure, poor adhesion between the adhesive layer and the second structure, poor consistency, e.g., excessive porosity, of the adhesive material itself, voids in the adhesive layer, or a combination of such conditions. By determining the specific location and nature of a bond fault, an inspection can permit an accurate diagnosis of the bonding problem and thus permit an appropriate adjustment of the bonding process to correct the particular difficulty. Without such specific information, it may be necessary to perform time-consuming, additional testing, and wasteful, destructive testing of a sampling of the manufactured output may be required.

In certain of the existing testing devices, a burst of ultrasonic energy is transmitted into a bonded, composite construction through a column of quartz or plastic material, and a subsequent reflection of energy from within the composite construction is received and analyzed as to its amplitude and phase. It is known, for example, that a void in an adhesive layer will result in a reversal in the phase of the reflected ultrasonic energy, and that ultrasonic energy will be reflected more readily from a void area than from a properly bonded area because of changes in impedance at interfaces between materials of differing properties and because of possible subsequent vibration or "ringing" within the void area. Reflected, ultrasonic signals are also affected by a number of other factors, however, and attempts to translate the complex, reflected signals into reliable predictions of bond strength, apart from the presence of voids in the adhesive, have not been generally successful. That is, while such testing devices have been generally successful in detecting definite voids, apparatus for evaluating the strength of bonds having no significant voids but potentially having areas of poor adhesion have not been sufficiently reliable to permit their widespread acceptance, particularly in the testing of bonded structures for critical or high-stress applications. As previously suggested, no completely reliable means has been provided for determining which of several potential bond faults exists in a particular workpiece.

Because of physical characteristics inherent in many of the epoxy or other bonding materials used in joining metal parts, the preferred thickness of the cured layer of adhesive formed between adjacent parts often lies within a range of about 0.004 to 0.010 inches, and optimally may be about 0.004 to 0.005 inches. Accordingly, bursts or pulses of ultrasonic energy of one to five megaHertz, typical of some of the existing, reflective or echo producing, ultrasonic testing apparatus, cannot produce corresponding, discrete reflected pulses from specific interfaces between the adhesive layer and the adjacent workpieces. The wavelengths of such energy are quite short, and pulse sensing testing devices employed for evaluating an adhesive layer whose thickness is substantially less than the wavelength of the ultrasonic pulse cannot conveniently provide precise information about the depth within the bonded structure at which the bond is defective.

A further, practical difficulty present in existing ultrasonic bond testing equipment resides in the difficulty of ensuring that the ultrasonic transducer is directly coupled to the workpiece, whereby extraneous reflection and resonances between the transducer and the workpiece are avoided. This is typically accomplished by employing a plastic column extending between the ultrasonic transducer and the workpiece to be evaluated, and by applying a layer of oil to the end of the plastic column and the workpiece in order to avoid the existence of an air gap between the column and the workpiece. Such an air gap would represent a sharp change in impedance at the interface, which would result in the reflection of most of the injected ultrasonic energy from that interface rather than from the bond area. A problem present in existing systems is that it may be difficult to distinguish between ultrasonic energy reflected from such an inadvertently caused, external air gap and that reflected from the area of an air gap constituting a void in the adhesive layer, and a false indication of a bond fault may thus result.

It is, accordingly, a major object of the present invention to provide new and improved means and method for evaluating adhesive bonds.

Another object is to provide bond testing means and method which permit convenient and rapid, nondestructive testing of adhesively bonded structures, thereby making it possible to test 100 percent of the bonded joints of manufactured structures if required.

A further object is to provide such means and method which are reliably operable to detect bond faults, such as excessive porosity of an adhesive layer and poor adhesion between an adhesive layer and an adjacent part, wherein no void exists between the adhesive layer and the part.

Yet another object is to provide such a means and method which is capable of distinguishing between various types of bond faults and of denoting the specific, spatial location, within a composite construction, of a bond fault.

A still further object is to provide such a means and method in which a pulse of ultrasonic energy of a wave length at least as short as the thickness of the layer of adhesive and of a duration less than approximately 1.5 wave cycles is transmitted into a composite construction comprising first and second structures bonded together by an intermediate layer of adhesive, whereby discrete pulses of wave energy are reflected from the interface between the first structure and the intermediate adhesive layer and from the interface between the adhesive layer and the second structure, whereby evaluation of the respective bonds between the adhesive layer and each of the respective, adjacent structures may be accomplished.

A further object of the means and method is to provide a definitive indication that a test probe employed for directing the ultrasonic pulses into the workpiece is in low impedance acoustical connection with the workpiece when a test pulse is transmitted into the workpiece, whereby spurious, high amplitude reflected signals are not received from the interface between the probe and the workpiece because of possible irregularities in the alignment and positioning of the probe against the workpiece, and whereby accurate test data may thereby be consistently obtained.

Another object is to provide such a testing means which is of economically practical construction, being adapted for manufacture as a small and easily portable unit.

Other objects and advantages will be apparent from the specification and claims and from the accompanying drawing illustrative of the invention.

In the drawing:

FIG. I is a partially diagrammatic representation of the ultrasonic transducer employed in the bond testing apparatus and of an adjacent, bonded construction to be tested;

FIG. II is a block diagram of the circuit employed in one embodiment of the bond testing apparatus and including a block representation of the transducer of FIG. I;

FIG. IIIa is a graph representing the amplitude of a pulse of ultrasonic energy generated by the transducer;

FIGS. IIIb, IIIc, IIId, IIIe, and IIIf are graphical representations of the amplitudes of ultrasonic signals reflected from interfaces within the test piece under various respective bond conditions;

FIG. IV is a schematic diagram of the pulse generator, preamplifier, and first gated amplifier sections of the circuit of FIG. II;

FIG. V is a schematic diagram of the timing and control circuits of the circuit of FIG. II;

FIG. VI is a diagrammatic representation of the pulse forms generated at respective portions of the timing circuit during a period of time.

FIG. VII is a schematic diagram of the first peak detection circuit;

FIG. VIII is a schematic diagram of the analog divider section of the circuit of FIG. II;

FIG. IX is a block diagram of a circuit constructed according to a second embodiment of the invention;

FIGS. Xa, Xb, Xc and Xd together comprise a block diagram of a suitable circuit board interwiring diagram circuit board layout of the circuit of FIG. IX;

FIG. XI is a schematic diagram of the pulser (video frequency pulse amplifier) and gated amplifier sections of the circuit of FIGS. IX and Xa and Xb;

FIGS. XIIa and XIIb together comprise a schematic diagram of the power supply of the circuit of FIGS. IX and X;

FIG. XIII is a schematic diagram of the timing circuit section of the circuit of FIGS. IX and X;

FIG. XIV is a schematic diagram of the signal comparitor and video pulse with converter;

FIG. XV is a schematic diagram of the voltage to frequency converter or bond metal ratio counter;

FIG. XVI is a schematic diagram of the peak detectors and one of the voltage to frequency converters;

FIG. XVII is a schematic diagram of the metal bond ratio counter, display decoder driver;

FIG. XVIII is a schematic diagram of the pulse width integrator or thickness converter;

XIX is a timing diagram of the operation of the circuit;

FIG. XX is a schematic diagram of the video frequency timing circuit;

FIG. XXI is a schematic diagram of the pulse width integrator of the first embodiment;

FIG. XXII is a schematic diagram of the phase detection circuit of the first embodiment; and FIG. XXIII is a schematic and block diagram of the analog to digital converter, the decoder driver display circuit of the first embodiment.

With initial reference to FIG. I, a composite, bonded construction or test piece 10 to be evaluated comprises a first structure 11, which in the illustrated application comprises a first sheet of aluminum, bonded to a similar, second structure 12 by an intermediate layer 13 of an adhesive. Adhesives employed in the bonding of such aluminum parts may typically be epoxies. The first structure 11 thus has a first surface 14 facing outwardly with respect to the test piece 10 and a second surface 15 facing inwardly and having at least partial contact with the adhesive layer 13 (and having substantially uniform contact if the adhesive layer is consistently bonded to the first structure 11). The second structure 12 has a surface 16 facing inwardly or toward the first structure 11 and having at least partial contact with the layer of adhesive 13.

An ultrasonic, piezoelectric transducer 20 having a high resonant frequency, e.g., of about 20 megaHertz, is positioned adjacent the composite test piece 10 for generating a test pulse of ultrasonic energy and directing it into the test piece. The transducer 20 is highly damped internally so that a test pulse at least as short as approximately 1.5 wave lengths may be obtained, for reasons which will become apparent. Such transducers 20 typically include a piezoelectric element 21 bonded to a quartz crystal 22 and connected to electrical terminals 23 and 24, according to practices known in the art. The crystal 22 and piezoelectric element 21 are enclosed within a housing 25 within which damping material 26 is contained in physical contact with the piezoelectric element 21 for minimizing any vibration of the piezoelectric element and the crystal 22 subsequent to electrical exitation of the transducer, as discussed hereinafter. A suitable, commercially available transducer 20 is that manufactured by Panmetrics, Inc. of Waltham, Massachusetts as Model no. VIP-20.

While operation of the transducer 20 does not require any particular physical orientation, for covenience of description, directional terminology such as "upwardly," "downwardly facing," and the like will be used herein with respect to its application as viewed in FIG. I, i.e., as an instrument supported above a planar, horizontally extending composite test piece 10 for directing ultrasonic wave energy vertically downwardly toward the test piece. Accordingly, the first surface 14 of the first structure 11 and the surface 16 of the second structure 12 are considered to be upwardly facing surfaces, and the second surface 15 of the first structure 11 a downwardly facing surface.

The VIP-20 ultrasonic transducer 20 may be modified by the addition of a polystyrene delay column 27 bonded to the lower end of the quartz crystal 22, or opposite the piezoelectric element 21, for improving the acoustic coupling between the transducer 20 and the composite construction 10, as will be more fully discussed in the description hereinbelow of the operation of the transducer. For further improving the acoustical coupling between the transducer 20 and the test piece 10, a quantity of oil, not shown, is applied between the lower end of the delay column 27 and the test piece. The use of such a layer of oil is a practice known in the art and serves to prevent the existence of an air gap between the delay column 27 and the test piece 10 which could distort the test results, as will be more fully discussed.

Referring additionally to FIG. II, a pulse generator circuit 30, to be described, is electrically connected to the transducer 20 (FIGS. I and II) for exciting the piezoelectric element 21 (FIG. I). Referring to FIG. I, the piezoelectric element 21 is thereby caused to emit an ultrasonic pressure wave which causes resonant vibration of the quartz crystal 22 and results in a corresponding pressure wave being directed downwardly through the polystyrene column 27 into the composite test piece 10. As will be more fully discussed in a later section, the injected acoustical energy is partially reflected by portions of the composite test piece 10 offering impedance to the passage of the acoustic wave energy. At interfaces, within the composite test piece 10, between members of differing acoustical impedance, mirror images of the injected, ultrasonic pulses are reflected upwardly toward the transducer 20. Because the transducer 20 is in low impedance acoustical contact with the test structure 10, these reflected pulses are conducted successively through the delay column 27 and the quartz crystal 22 to the piezoelectric element 21, which produces electrical pulses corresponding to the reflected, acoustical pulses. The plastic delay column is advantageous, but not mandatory.

Referring now to FIG. IIIa, the preferred wave form of the ultrasonic pulse generated by the transducer (in response to a corresponding electrical pulse generated by the pulse generating circuit 30 to be described) is a sine wave of a wavelength shorter than the thickness of either the first structure 11 or the intermediate adhesive layer 13 and of a duration of one wave cycle. However, a generated pulse of a duration as long as approximately 1.5 wave cycles may be successfully employed, for reasons which will become apparent. When the generated pulse reaches the interface between the polystyrene delay column 27 and the composite construction or test piece 10, a substantial proportion of the ultrasonic energy passes into the test piece 10 because of the low impedance connection between the delay column 27 and the first structure 11 (FIG. I).

Referring primarily to FIG. II, the pulse generating circuit 30 (FIGS. II and IV) is triggered by signals generated by the timing and control circuit 31 (FIGS. II and VI), all to be described. Referring to FIG. II, a low voltage power supply circuit 32 is employed for generating a positive, 5 volt DC output at terminal 34 and positive and negative, 12 volt DC power outputs at terminals 35 and 36, respectively. A suitable, commercially available power supply providing the +5V output is Model 2B5−3 of the Powertec company, and a second unit for providing +12V DC and −12V DC is Model 2K 15D−1.3 of Datel Systems, Inc. of Canton, Massachusetts. A high voltage power supply 40, suitably a DC to DC converter unit available as Model HC-4301 of Technetics, Inc. of Boulder, Colorado is also employed, receiving +12V DC from the low voltage power supply, and providing a +250V DC output at terminal 41.

Referring additionally to FIG. IV, the 250V output terminal 41 is connected to the pulse generating circuit 30 through lead 42 connected to an RC network comprising a resistor 43, of about 47 kilohms, and a capacitor 44 of about 25 picofarads connected in series with the resistor 43. The input lead 42, resistor 43, and capacitor 44 are serially connected, a terminal 45 being connected between the resistor 43 and the capacitor 44. The opposite side of the capacitor 44 is connected to a terminal 46 connected to the non-grounded side of a coaxial connector 47 which in turn is connectible to the center lead of a flexible coaxial cable 48 which extends to the transducer 20 (FIG. I), the center lead being connected to the non-grounded terminal 24 of the piezoelectric element 21 of the transducer 20 (FIG. I). The grounded terminal 24 of the transducer 20 is connected through the external or grounded conductor of the cable 48, through the coaxial connector 47, to a grounded lead 50.

An NPN switching transistor 51, suitably a 2N3501, has its collector connected to the terminal 45 and its emitter connected to the grounded lead 50. The switching transistor 51 is normally non-conductive and biased slightly negatively with respect to ground lead 50. A 5,000 ohm potentiometer 52 which receives a negative potential, from the −12V supply terminal 36, has its variable voltage output fed through a 10,000 ohm resistor 53 to a terminal 54 connected through a 100 ohm resistor 55 to the base of the switching transistor 51. The 10,000 ohm resistor 53 is provided for limiting the reverse bias supplied to the base of the transistor 51 for preventing possible damage from current overloads. The terminal 54 connected to the 100 ohm resistor 55 is also connected to the input of an RC network comprising a 4,700 ohm resistor 56 and a parallel capacitor 57, which is suitably of approximately 200 picofarads, the other common connection of the RC network being connected to an input terminal 60 which, during operation of the circuit, receives positive pulses, at regular intervals, from a portion of the timing circuit 31 to be described. The triggering pulses are suitably of approximately 2.5 to 4.5 volts DC, according to practices commonly used in providing input signals to transistor logic circuitry. Upon the reception of one of these regularly spaced pulses passed through capacitor 57, the switching transistor 51 is made conductive, whereupon the terminal of the capacitor 44 connected to terminal 45 becomes negative with respect to its other side connected to the terminal 46. The terminal 46 is normally maintained at ground because of its connection through a high value resistor 59, suitably of approximately 20,000 ohms, to the grounded lead 50. Upon the transistor 51 becoming conductive, terminal 46 suddenly becomes negative in value, receiving the stored charge from capacitor 44; and because terminal 46 is then of a greater negative potential than the grounded lead 50, a spike or sudden surge of potential is placed across the coaxial cable 48 and the transducer 20 (FIG. I) causing the transducer to direct a corresponding pulse of ultrasonic energy into the composite test piece 10.

With continued reference to FIG. IV, a coupling capacitor 61 is connected between the terminal 46 and the preamplifier section 62, to be described. For preventing damage to the preamplifier circuit from the initial pulse transmitted to the transducer 10, first and second, limiting diodes 63, 64, suitably 1N270 types, are connected in inverse parallel between the grounded lead 50 and a signal carrying lead 65 for limiting the voltage which may appear between the two leads 50, 65 during pulse transmission to the transducer 20 (FIG. I). The diodes 63, 64 operate in conjunction with a voltage dividing resistor 66 of approximately 620 ohms connected in series between the coupling capacitor 61 and signal carrying lead 65.

In operation of the pulse generator circuit 30, the time consonant of the RC circuit comprising capacitor 57 and resistor 56 is shorter than the duration of one wave cycle of the transducer 20 at its resonant frequency which may be of the order of 25 $MH_z$, so that the ultrasonic pulse generated thereby is essentially a single wave cycle in length, as preferred. The length of the emitted pulse is also governed by the adjustment of the potentiometer 52, and by the damping material 26, or by the natural resonance of the transducer 20. Referring now to FIG. IIIa, the electrical pulse 70 applied to the transducer 20 is initially negative and subsequently positive, and it is of the order of about 30 volts in magnitude. Referring to FIG. I, as the emitted ultrasonic pulse successively strikes the three respective interfaces (1) between the transducer 20 and the first surface 14 of the first structure 11; (2) between the first structure and the adhesive layer 13; and (3) between the adhesive 13 and the second structure 12, respective ultrasonic pulses are reflected upwardly toward the transducer 20. The delay column 27 serves to cause a delay between the transmitted pulse and the reception by the piezoelectric element 21 of these three successive, reflected pulses for permitting the transducer 20 to damp or recover from its vibratory, transmitting state. The transducer 20 is then responsive to the reception of the three reflected ultrasonic pulses, and upon their reception by the piezoelectric element, respective electrical pulses corresponding to the three reflected pulses are generated across the coaxial cable 48. Referring additionally to FIG. IIIb, these electrical pulses corresponding to the successively received, acoustical pulses, consist of the first pulse 71 corresponding to the acoustical pulse received from the interface between the delay column 27 and the first surface 14 of the first structure 11, a second pulse 72, normally inverted, received from the interface between the first structure 11 and the adhesive layer 13, and a third pulse 73, again normally inverted, corresponding to the pulse received from the interface between the adhesive 13 and the second structure 12. The three pulses are of decreasing magnitude, and the first may be of the order of approximately 4 volts.

Referring again to FIG. III, and secondarily to FIG. II, the preamplifier section 62 is provided for receiving the low voltage pulses, referred to herein as the "received" pulses, generated by the piezoelectric element 21. Because the spacing between the successive, received pulses may be very short, the preamplifier 62 must be capable of operation at frequencies in the order of 20 megaHertz or higher, and dual video frequency amplifiers 74, 75 are employed in series. The video frequency amplifiers 74, 75 are suitably of a type manufactured by Motorola Semiconductor Products, Inc. as part number NC1590G. These video frequency amplifiers 74, 75 are differential amplifiers having their inputs connected across inputs from the negative lead 50 and signal carrying leads 76 and 77. The signal carrying lead 76 to the first amplifier 74 is connected in series with a 1.0 microfarad coupling capacitor 78 which has its other side connected via signal carrying lead 65 to the pulse generator 30. The non-inverting input of the first operational amplifier 74 is connected through parallel capacitors 79 and 80, of respective values of 1.0 and 0.001 microfarads, to the grounded lead 50. The first operational amplifier 74 receives positive 12 volt supply power from the +12V supply terminal 35 through a decoupling resistor 81 of approximately 270 ohms which is connected to a power supplying lead 82. The first amplifier 74 is grounded through lead 83 connected to the ground lead 50, and a biasing resistor 84 of approximately 5,600 ohms is connected between pin 2 of the first operational amplifier and the grounded lead 50. Output terminals 5 and 6 of first amplifier 74 provide an output comprising a differential voltage amplified from that received across input terminals 1 and 3. Terminal pin 7 of the amplifier 74 is connected to the power supplying lead 82 and connected to the grounded lead 50 through capacitor 85. Biasing resistors 86 and 87 are connected between power supplying lead 82 and output leads 88 and 89 from the first amplifier 74. The output signals from terminals 5 and 6 of the first amplifier 74 are conducted through leads 88 and 89, through respective coupling capacitors 90 and 91 of approximately 1.0 microfarads, to the input terminals of the second operational amplifier 75. Terminals 7, 2, and 4 of the second video frequency amplifier 75 are connected as were those of the first video frequency amplifier 74, and output terminal 6 is connected to the power supplying lead 82. Output terminal 5 is connected through lead 92 to a load resistor 93 of approximately 2,000 ohms which is also connected to the power conducting lead 82; and a coupling capacitor 94 is connected to the output lead 92 in series with an output terminal 95. Output terminal 95 is connected to the first gated amplifier 96 (FIGS. IV and II), and to the second and third gated amplifiers 97, 98, as shown in FIG. II.

With continued reference to FIG. IV, the output terminal 95 of the preamplifier circuit 62 is conducted via lead 100 to one side of the first gated amplifier section 96 (FIGS. IV and II). The lead 100 is connected through a coupling capacitor 101, of about 0.001 microfarads, to the non-inverting input 102 of channel 1 of a two channel, wide band, gated video frequency amplifier 104 such as model MC1445G manufactured by Motorola Semiconductor Products, Inc. The inverting input terminal 103 of the first channel of the gated amplifier 104 is connected through a coupling capacitor 105 of approximately 0.001 microfarads to a lead 106 which is connected to the grounded lead 50, so that a differential voltage is applied across the two inputs 102, 103 of the first channel corresponding to the voltage differential between the grounded lead 50 and the output 95 of the preamplifier stage 62. A gate terminal 107 of the gated amplifier 104 is connected by lead 108 to an output terminal 110 of the timing circuit 31 (FIG. V) to be described, the timing circuit being operable to supply a gating potential to the gate terminal 107 during a particular time period which corresponds to the time period during which a reflected signal (71, FIG. IIIb) may be received by the transducer 20 (FIG. I) from the first interface, i.e., that lying between the transducer and the first structure 11. Power input terminals 111, 112 of the operational amplifier 104 are connected respectively to a lead 113 connected to the +12 volt supply terminal 35 and to a lead 114 connected to the −12 volt output 36 of the low voltage power supply 32 (FIG. II). The second channel of the gated amplifier 104 has its non-inverting input 115 connected to the grounded lead 106, and its inverting input 116 is connected to the variable output terminal 117 of a voltage divider 118 connected serially across the positive and negative power supplying leads 113 and 114. In operation, the second input channel 115, 116 of the gated amplifier 104 receives an input signal from the voltage divider 118 which may be adjusted to equal that normally received from the output terminal 95 of the preamplifier circuit 62 when there is no signal received from the transducer 20. Thus, when the gated amplifier section 96 switches from the second to the first input sections when no output signal is received from the preamplifier 62, there is a smooth transition, rather than a variation in output caused by a marked difference in input levels; and, upon a pulse being received from the transducer 20 resulting in a variance in the output voltage from the preamplifier stage 62, the gated amplifier 104 emits an amplified pulse corresponding to the voltage differential across its first stage input terminals 102, 103, which output signal is conducted to output terminal 123.

With primary reference now to FIG. V, terminal 123 is connected to one side of a first NOR gate 163, which is suitably a 7402 integrated circuit. The first NOR gate 163 is a part of the gating circuit 125 illustrated in FIG. V in association with the timing circuit 31. Description will now be made of the timing circuit 31 itself in order that the operation of the gating circuit 125 in conjunction therewith may be more readily understood. The timing circuit 125 is driven by a one-megaHertz oscillator 126, which is preferably a temperature controlled, crystal oscillator circuit, such as that available from the Connor-Winfield Corporation of Winfield, Illinois as model C12. The power inputs of the oscillator are respectively connected to ground and to the +5V supply output 34. The output lead 127 from the oscillator 126 is fed to the first of a series of decade counters such as those manufactured by the Signetics Corporation under model number N74192, of which seven (first, second, third, fourth, fifth, sixth, and seventh counters 130, 131, 132, 133, 134, 135, and 136) are employed in series. The output from the oscillator 126 is connected to the "count up" input 140 (pin 5) of the first decade counter 130. The D stage output 141 of the counter 130 (terminal 7) is in turn connected to the "count up" input 142 of the second counter 131, whose output is connected similarly to the "count up" input of the third decade counter 132, and so on. As understood by those in the art, the outputs of the respective, successive decade counters will thus comprise rectangular pulses of increasing duration. Referring now to FIG. VI, wave form 143 represents the output, comprising rectangular pulses of one megaHertz frequency, from the oscillator 126 (FIG. V). Wave form 144 represents the "C stage" output of the first decade counter 130, having positive pulses lasting for 4 microseconds, spaced apart by time sequences of 6 microseconds. Wave form 145 represents the "D stage" output of the first decade counter 130 and comprises positive rectangular pulses of 2 microseconds spaced apart by intervals of 8 microseconds; and wave form 146 represents the output of the A stage output of the second decade counter 131 and comprises positive pulses of 10 microseconds beginning at the ends of the 2 microsecond pulses of wave form 145 and separated by intervals of 10 microseconds.

Referring again to FIG. V, the A stage output of the second decade counter 131 is conducted via leads 150 and 151 to terminal 60 which represents the trigger input terminal 60 of the pulse generating circuit 30 (FIG. IV). The input terminal 60 is connected to the base of the switching transistor 51 which initiates the emitted pulse of the transducer 20. Referring to FIG. VI and to wave form 146, the rectangular pulses emitted by terminal $a_2$ of counter 131 occur every 20 microseconds. Point 152 is therefore the beginning of a first firing sequence of transducer 20, and point 153, is the beginning of a second firing sequence 20 microseconds later. For a period of 4 microseconds after each of these time points 152, 153, however, the first gated amplifier 96 (as well as gated amplifiers 97 and 98) are turned OFF until the C stage output 144 via lead 145 from the first counter 130 is turned ON or positive (e.g., as at point 154) whereby input signals are applied simultaneously to the two input terminals 155, 156 of an AND gate 157 (FIG. V) in the gating circuit 125. The AND gate 157 may suitably be an N7421 gate, available from the Sinetics Corporation. The output from the AND gate 157 is fed via lead 160 to the clocking input of a 7474 latching or dual, type D latching circuit (referred to hereinafter as the first latching circuit 161). The D input of the latching circuit 161 receives a positive bias from the +5V power supply terminal 34 through a protective, 1K ohm resistor 162, and the Q output is connected to terminal 110, which in turn is connected to gate control terminal 107 of the gated operational amplifier 104 of the first gated amplifier circuit 96 shown in FIGS. IV and II.

In operation, upon the AND gate 157 receiving positive signals from both the first and second decade counters 130, 131, the AND gate 157 is turned ON or conductive, turning ON the first latching circuit 161, whereby a positive gating signal is conducted via lead 108 (FIG. IV) to the gate 107 of the first gated amplifier 104 to permit its amplification of a first reflected pulse (pulse 71 of FIG. IIIb). Thus, the gated amplifier section 96 is turned OFF for a 4 microsecond period after the initiation of the firing sequence, whereby the firing pulse is not passed by the gated amplifier section 96, and whereby spurious signals generated by the transducer 20, because of possible internal resonance after the firing pulse, are not passed by the amplifier section 96. Within a few nanoseconds after the reception of the first received pulse 71 (FIG. IIIb), depending upon the thickness of the first structure 11 and upon the velocity of acoustic waves within the particular material of the first structure, the second pulse 72 is received from the transducer 20 and amplified by the preamplifier circuit 62, whose output at terminal 95 is fed to the first, second and third gated amplifiers 96, 97, and 98 (FIG. II). The output from the first gated amplifier 96 from the first received pulse 71 is applied to terminal 123 which (referring now to FIG. V) feeds one side of a first, 7402 NOR gate 163 whose output is connected by lead 164 to the reset terminal of the first latching circuit 161. Because the NOR gate 163 is operable to emit a negative output if a positive bias is received at either of its input terminals, the positive pulse received from the terminal 123 from the first gated amplifier 96 causes the gate 163 to apply a negative bias to the latching gate of the first latching circuit 161. This negative input to its latching terminal causes the first latching circuit 161 to be reset, causing its "Q-not" terminal 170 to have a positive bias. Terminal 170 is connected to the clocking input terminal 171 of a second 7474 latching circuit 172, and the positive signal input applied to terminal 171 is thus effective to turn the second latching circuit 172 ON. The second latching circuit has its D input connected to the +5V terminal 34 as was the first latching circuit 161. The second latching circuit 172 has its Q output 173 connected by lead 174 to the gate control terminal of the video frequency amplifier of the second gated amplifier 97 (FIG. II), whose circuitry is identical to that shown in FIG. III for the first gated amplifier 96 and is therefore not shown in detail in the drawing. The output of the second gated amplifier 97 thus contains an amplified signal corresponding to the second reflected pulse 72 and is conducted to terminal 175 (FIGS. II and V). As shown in FIG. V, terminal 175 is connected by lead 176 to a second NOR gate 180, identical to the first NOR gate 163. This signal causes the second NOR gate 180 to emit a negative bias voltage through its output lead 181, which is connected to the latching reset terminal of the second latching circuit 172, causing the second latching circuit 172 to reset and emit a positive voltage at its $\overline{Q}$-not terminal 182. $\overline{Q}$-not terminal 182 is connected to the clocking input terminal 183 of a third latching circuit 184 whereby the third latching circuit is made conductive by the positive input signal, supplying a positive gating voltage through lead 185 to the third gated amplifier section 98 (FIG. II). The positive gating voltage on lead 185 is fed to the gated video frequency (not shown) of third gated amplifier section 98 in a manner corresponding to that previously described with respect to the gated operational amplifier 111 of the first gated amplifier 96 (FIG. III), turning the third gated amplifier 98 ON, or conductive, for receiving and amplifying the third reflected pulse 73 (FIG. IIIb), which is received from the interface between the adhesive layer 13 and the second structure 12. The output signal of the third gated amplifier section 98 is conducted to terminal 186. Referring to FIG. V, terminal 186 is connected to the non-common input of a third 7402 NOR gate 187, whose output is conducted via lead 188 to the reset terminal of the third latching circuit 184, whereby the third latching circuit 184 is reset and the third gated amplifier circuit 98 is again turned OFF.

To prevent the occurrence of an open latching circuit, e.g., because of nonreception of a returned pulse from any one of the interfaces, a gate resetting provision is provided occurring at 10 microseconds after the opening of the first gate 96, e.g., at point 189, FIG. VI.

A common lead 190 which is connected to the common input terminals of the first, second, and third NOR gates 163, 180, and 187, is connected to the output terminal of a fourth NOR gate 191, also suitably a 7402 gate module, whose inputs are connected to leads 192 and 193. A 7404 inverter 194 is connected between the lead 193 and terminal 195, connected to the C stage output 145 of the first decade counter 130. Lead 192 is connected to terminal 196, which is connected to the A stage output of the second counter 131. Thus, upon the reception of a negative bias at terminal 196 and a positive bias at terminal 195 from the counters 130, 131, negative biases are applied to both inputs of the fourth NOR gate because of the inverter 194, causing the fourth NOR gate 191 to emit a positive output to the common lead 190. This causes the output of the first NOR gate 163 to go low, resetting the first latching circuit 161 and causing the second and third latching circuits 172, 184 to sequentially reset, making the circuit ready for the next received pulse.

This resetting caused by the fourth NOR gate 191 occurs upon the reception of a negative bias through lead 150 from the A state output of the second decade counter 131 (as beginning at time point 197, FIG. VI), and upon the reception of a positive bias from the C stage output 145 of the first decade counter 130 which occurs 10 microseconds following the initial positive pulse (as shown at time point 189 on wave form 144 of FIG. VI).

With respect now to the output from the first gated amplifier 96 which is conducted to terminal 123 (FIG. II), a first peak detection circuit 200 is provided having its input connected to terminal 123 for responding to a positive pulse above a predetermined amplitude. Second and third peak detection circuits 201, 202, identical to the first peak detection circuit 200, have their inputs connected to terminals 175 and 186, respectively, which receive the output signals from the second and third gated amplifiers 97, 98. Referring now to FIG. VII, terminal 123 is connected to the base of an NPN, buffering transistor 203, suitably a 2N5368 transistor, whose collector is connected through a 680 ohm resistor 204 to a positive, low voltage supply lead 205 connected to the +12V supply voltage terminal 35 from the power supply 32 (FIG. II) and whose emitter is connected through a resistor 206 of approximately 510 ohms to the inverting terminal 207 of a high frequency response, operational amplifier 210. The operational amplifier 210 is operational at frequencies up to 10–100 megaHertz, and is suitably an A502 unit as manufactured by the Intronics Company. The emitter terminal of the transistor 203 is connected through a capacitor 211 of approximately 5.0 picofarads to a grounded lead 212 for passing high frequency (noise) signals to prevent amplification by amplifier 210 of such noise and to improve the signal/noise ratio. A biasing resistor 213 of about 15 kohms is connected between the base of the transistor 203 and the grounded lead 212, and a coupling circuit comprising a 2,000 ohm limiting resistor 214 connected in parallel with a capacitor 215 of approximately 68 picofarads is connected between the base of the transistor 203 and terminal 123. The limiting resistor 214 serves to protect the transistor 203 from excessive input signals, and the 68 picofarad capacitor 215 passes the momentary pulses received from the first gated amplifier 96 but does not pass DC or low frequency signals. The high frequency operational amplifier 210 has its positive power input terminal connected to the +12V supply through leads 216 and 205 and its negative power input connected to the −12V supply through lead 217 and −12V supply lead 220. The inverting input 221 of the operational amplifier 210 is connected to the grounded lead 212. The balance terminal 222 of the operational amplifier is connected to the moving contact 223 of a 50 kohm voltage divider 224, which is connected across the +12V and −12V carrying leads 205 and 220, the voltage divider 224 providing a means for varying the balance of the operational amplifier 210 in order to zero its output when it receives no input signal.

The operational amplifier 210 serves to invert the polarity of its input signal, and is operable to emit a negative output upon the reception of a positive input corresponding to the positive leg of the pulses 71, 72, and 73 as shown in FIG. IIIb. An 1N914 feedback diode 225 is connected between the output terminal of the operational amplifier 210 and its inverting input 207 for preventing the occurrence of a positive output from the operational amplifier 210, or so that the output corresponds only to the positive leg of the received pulses. A second 1N914 diode has its cathode connected to the output 226 of the operational amplifier 210 and its anode connected to a lead 230 which is connected to a feedback loop including a first resistor 231 of approximately 1.2 kohms and a second resistor 232 of 560 ohms, for cooperating with the resistor 206 of 510 ohms for setting the gain of the operational amplifier 210. A detecting section 233 comprises a diode 234, suitably an 1N914 diode, having its cathode connected to the output lead 230 from the amplifier 210 and its anode connected via lead 235 to the base of a PNP transistor 236, suitably an MPS6519, serving as a buffer between the detector section 233 and the output stage 237. A capacitor 240 of approximately 0.001 microfarads is connected between the lead 235 and the ground lead 212. Upon the reception of a negative pulse from the operational amplifier 210, the lead 235 carries a potential below that of the grounded lead 212, and the capacitor 240 is charged negatively.

An output stage, operational amplifier 241, suitably a 747, has its inverting input terminal 242 connected through a resistor 243 of approximately 5.1 kohms through a diode 244 (1N914) to the emitter terminal of the PNP transistor 236. The emitter terminal of the transistor 236 is also connected through resistor 245 of about 1.2K ohms to the +5V supply terminal 34. Thus, the emitter terminal of the transistor 236 is normally maintained at a positive level which prevents any output through the output stage operational amplifier 241. Upon the occurrence of a negative potential across the capacitor 240, the transistor 236 becomes proportionally more conductive, eventually causing the emitter terminal to become of negative polarity, causing the output operational amplifier 241 to be biased ON. The integrating circuit comprising the diode 234 and the capacitor 240 is provided for integrating the number of pulses and the pulse heights of pulses occurring during a predetermined time period, i.e., the 10 microsecond pulse spacing, whereby the output of the output transistor 236 represents a signal proportional to the average pulse height received during the 10 microsecond period. A resistor 246 of approximately 10 kohms is connected across the output operational amplifier 241 to adjust its gain, in conjunction with the resistor 243 of approximately 5.1 kohms. The noninverting input 247 of the amplifier 241 is connected through a resistor 250 of approximately 3.3 kohms for referencing the noninverting terminal at an appropriate level.

The output of the operational amplifier 241 is connected by lead 251 to output terminal 252 (FIGS. VII and II), and the output signal applied thereto is thus a DC level corresponding to the average height of the first received pulses 71 (FIG. IIIb) received during each 10 microsecond interval. Similarly, the output signal from the second peak detector circuit 201 corresponds to the average height of the second received pulses 72 (FIG. IIIb) received during the same time period.

The outputs of the first and second peak detector circuits 200, 201 are connected to a first analog divider circuit 253 (FIGS. II and VIII for computing a ratio of the output signals from the peak detector circuits 200, 201. Referring now to FIG. VIII, the output of the second peak detector circuit 201 (FIG. II) is connected via lead 254 to an input resistor 255 of approximately 10,000 ohms which in turn is connected to the inverting input of an operational amplifier 256, such as model LM101 manufactured by the Sinetics Corporation. The operational amplifier 256 comprises a first logrithmic amplifier for converting the analog output of the second peak detector circuit 201 into a logrithmic output. A frequency compensation is provided by a feedback capacitor 257 of approximately 300 picofarads. An appropriate ground signal reference level is supplied to the noninverting input by resistor 260 of approximately 10 kohms. The above described section comprises a first log amplifier section 261 of the circuit 253, a similar, second log amplifier section 262 is connected to terminal 252 which receives the output signal from the first peak detector circuit 200 of FIG. II. The second log amplifier section 262 includes an input resistor 263, operational amplifier 264, feedback capacitor 265, and resistor 266, which are interconnected as are the corresponding components of the first log section 253. The output terminals of the operational amplifiers 256, 264 are connected through respective 1 kohm resistors 270, 271 to respective output terminals 272, 273. First and second NPN logging transistors 274, 275, suitably 2N3728's in a matched pair, have their emitters connected to terminals 272 and 273, respectively, and their collectors connected to the inverting inputs of the first and second operational amplifiers 256, 264, respectively. The base voltage of the second logging transistor 275 is derived from a reference voltage supplied from the +12V supply 35 connected through a bridge network 276 including parallel 10 kohm resistors 280, 281, 10 ohm potentiometer 282 connected to the Zener diode 283, suitably an LM 103, which is connected to ground. The base voltage of the first logging transistor 274 is connected through lead 284 and through third logging transistor 285 to terminal 286, which is connected through 10 kohm resistor 287 to receive a reference voltage provided by voltage divider 288 connected between the 12 volt supply terminals 35, 36. A third LM101 operational amplifier 290 operates in conjunction with the logging transistor 285 fed by the input from the voltage divider 288 for logging the input signal set by voltage divider 288, and the output of this stage is connected to the base of first logging transistor 214 for adding this signal to the output of the first log amplifier section 261. The summed output at terminal 272 is being divided by that of the second log amplifier section 262 by an antilog generator section 292 which includes an LM101 operational amplifier 293 for generating an output which is equal to the product of $E^2$ times $E^1$ divided by $E^3$. The operational amplifier 293 is frequency compensated by shunt capacitor 294 of approximately 30 picofarads. The output of operational amplifier 293 is conducted via lead 25 to the analog multiplexer 400 (FIG. II) which is suitably a module model MM8 manufactured by the Datel Stems (Datel Systems) Company. A second analog divider circuit 420 identical to the analog divider circuit 253 and therefore not shown in detail is connected to receive the output signals from the third peak detect circuit 202 at one of its log amplifier sections and to receive the output fed to common terminal K at its other log amplifier section (not shown) and is operable to provide an output signal proportional to the quotient of signal 3 divided by signal 1. Accordingly, the output from the first analog divider 253 is a signal which corresponds to the ratio between the amplitudes of the first and second reflected pulses, and the output of the second analog divider circuit 420 corresponds in amplitude to the ratio between the first and third reflected pulses.

Blocks 172 and 184 of FIG. II correspond to the second and third flip flop latching circuits of FIG. V; i.e., they serve not only to sequentially gate the gated amplifiers 1, 2, and 3 (96, 97, and 98) but also to receive the outputs from the gated amplifiers from points 294, 295, and 296. The second latching circuit 172 produces an output corresponding in length to the time difference between the reception from the first gated amplifier output indicative of its reception of the pulse from the first reflected pulse and to lasting until a pulse is received from the second gated amplifier indicative of its reception of a pulse corresponding to the second reflected pulse. The latching circuit 184 produces an output corresponding to the time difference between the reception by gated amplifier number 2 of the second reflected pulse signal and lasting until the third gated amplifier produces an output indicative of its reception of a signal indicative of the third reflected pulse being received. Referring now to FIG. XXI, the timed pulse emitted by the time difference latching circuit 172 is fed to a pulse width integrating circuit 300 for generating a pulse of an amplitude corresponding to the pulse width received. The input circuit is fed through lead 301 to a limiting circuit comprising a 2.7K ohm resistor 302 connected in parallel with a 200 picofarad capacitor 303 to the base of an amplification stage comprising NPN transistor 2N5368 304 whose emitter is connected to ground and whose collector is connected to the +12 volt power supply outlet through a load resistance section comprising resistors 305 and 306, each of approximately 10K ohms. The output is taken from between these two resistors 305 and 306 to the base of a PNP transistor 308 suitably a 2N2907 whose collector is connected to ground and whose emitter is connected through a 4.7K ohm resistor 307 to the 12 volt positive supply. An integrating section 317 is provided comprising of a second 2N2907, PNP transistor 309 whose base is connected to the emitter of PNP transistor 308 and its collector is connected through a forwardly biased diode IN914 313 for passing only positive signals to the integrating capacitor 389, suitably a 200 picofarad capacitor whose opposite side is connected by lead 315 to ground in which capacitor 389 serves to integrate the output signals from transistor 309. The collector of the transistor 309 is biased by resistor 314 which is connected between it and ground and is suitably of approximately 470K ohms. The current gain of transistor 309 may be adjusted by means of a voltage dividing circuit comprising resistor 310 of 2.7K ohms connected in series with variable resistor 311 of 2K ohms to the +12 volt supply. Potentiometer 311 permits adjustment of the circuit to calibrate the analog output of the integrator. The integrating circuit is connected by lead 317 to the input of a peak detection circuit 318 (FIGS. XXI and II). The operation of the peak detection circuit is similar to that previously described; it is operable to emit a constant DC voltage in the presence of pulses received from the pulse width integrating circuit 300 of predetermined amplitudes. The outputs of the first and second peak detection circuits are fed to inputs 1 and 2 of the analog multiplexer 400 (FIG. II) and the outputs of the first and second analog dividers 253, 420 are fed to the third and fourth inputs of the multiplexer 400. Thus, the signal fed to input 1 is an analog voltage corresponding to the time difference between signals 1 and 2, that to input 2 is an analog voltage corresponding to the time difference between signals 2 and 3, that applied to input number 3 is an analog voltage corresponding to the ratio of the amplitude of signal number 1 to signal number 2 and that applied to input number 4 is an analog voltage corresponding to the ratio of amplitudes of signal number 3 divided by signal number 1. The analog multiplexer serves to sample these voltages at successive, equal time periods of approximately 40 microseconds as commanded through the input of address control through the channel selection command cable 401 connected to the control circuit 31 of FIGS. II and V. Referring now to FIG. V, the multiplexer control leads 208 and 197 are connected to the Q outputs of respective 7474 latching circuits 198 and 199, the second latching circuit 199 having its clock input connected to the $\overline{Q}$ - NOT output of the first latching circuit 198. The data input of the first latching circuit is connected by lead 463 to the $\overline{Q}$ - NOT output of the first latching circuit and the second latching circuit is similarly connected to a feed back lead 464. Second and third 7474 flip flop circuits F and G have their reset terminals connected to the lead (a) connected to the megaHertz oscillator 126. The clocking input of the second flip flop circuit G is connected by lead 11 to the $D^2$ output of the second decade counter, and the locking input of the first latching circuit (flip flop circuit) is connected by a lead 127 to the $C^2$ terminal of the second decade counter, and the D inputs of both latching circuits are connected through a 1K resistor i to the +5 volt DC power supply output. The $\overline{Q}$ - NOT outputs of each of the latching circuits are connected to respective inputs of a 7400 NAND gate j, whose output is connected to the clock input of the first clock input of the pairs 198 and 199. As will be understood by those in the art, the output of the NAND gate which is derived from this particular combination comprises a series of pulses occurring every 40 microseconds, and the two flip flop circuits 198 and 199 produce a series of multiplex control circuits every 40 microseconds which serve as computer command inputs to the analog multiplexer 400 (FIG. II) causing it to select sequentially the first, second, third and fourth input channels once changing every 40 microseconds.

To review the operation of the circuit, the reflected signals are received from the transducer, amplified in the preamplifier, and routed to the inputs of the three gated amplifiers. After the initial, transmitted pulse, the first amplifier is gated so that signal number 1 is allowed through. The occurrence of signal 1 closes the gate for the first amplifier and opens the second amplifier. In like manner, the reception of signal number 2 closes gate two and opens gated amplifier three. When signal number 3 is received, gate 3 is closed. This sequence is repeated each time the transducer is pulsed. The positive pulses from each gated amplifier are routed to peak detector and hold amplifiers which provide a DC level corresponding approximately to the average amplitude of the respective pulses. These voltages are routed to the analog divider circuits with the resulting voltage corresponding to the ratio of signal number 2 to signal number 1 and the ratio of signal number 3 to signal number 1. These voltages are routed to the multiplexer, which selects an analog signal for conversion to a digital (3 digit, binary coded decimal) signal. The digital signal is stored in the 12-bit latch which holds the signal for display. (The reason for excess sample rates is that it provides the potential of scanning at higher rates if required in other modifications of the circuit.)

Considering now the outputs from the gated amplifiers, signal 1 sets the time difference bistable multivibrator (flip-flop) which is reset when signal number 2 is received. The resulting pulse width corresponds to the time it takes the pulse to travel through the first metal structure 11 and return from its interface with the adhesive 13. This time can be converted to metal structure 11 thickness. The pulse width is processed in the fast integrating pulse width integrater circuit to convert pulse width to pulse height, and the associated peak detection circuit is again used to provide an analog voltage which is converted to a display in the same manner as the amplitude displays. The time difference between signal number 2 and signal number 3 provides the corresponding thickness of the adhesive layer 13.

The output of gated amplifiers number 1 and number 3 are used in the phase reversal detection circuit. Phase reversal of signal number 1 indicates that the transducer is not in good contact with the first structure 11. When this condition occurs, the red lamp is illuminated and the displays are disabled. Phase reversal of signal number three indicates that a void exists in the adhesive layer. The red lamp indicating second interface void is illuminated but the displays remain active.

The clock and control circuitry provides the control sequence to initiate the pulse, gate the amplifiers, command the analog to digital conversion, select the analog signal to be converted, and strobe the displays.

Referring to FIG. XII for a description of the phase reversal detection circuit. The output of the gated amplifier is connected via a 1200 ohm resistor into two threshold circuits, 2N5368 transistors. The potentiometer is used to adjust the base of the transistor Q1 below cutoff until signal 1 occurs. If signal 1 is positive initially transistor Q1 turns on and the voltage to gate 7402 goes low. If the other input to the gate is low the output goes high. This is a positive NOR gate such as SN7402 manufactured by Texas Instruments, Inc. When the gate output goes high, the latch goes high. The latch is a D-type positive-edge-triggered flip-flop such as SN7474 manufactured by Texas Instruments. The not true output goes to AND gate such as SN7408. Transistor Q2 is biased with the potentiometer so that it is turned on. When a negative transition occurs on the input, transistor Q2 is turned off so that the input to gate SN7408 goes high and will be latched if the upper latch has not been activated first. The not true output of the latch is routed through gate SN7400 so that the transistor controlling the red lamp is lit. Therefore, if the positive transition occurs first the lamp status does not change (the green lamp stays lit); if the negative transition occurs first the red lamp will light. Pressing the lamp test push button applies a ground to both gates, thus turning on both lamps and blanking the displays.

Phase reversal for signal number 3 is implemented in the same manner except that the numeric displays are not blanked.

The output from the gated amplifier goes to a peak detector circuit shown in FIG. VII. The input circuit is an emitter-follower using a 2N5368 transistor. The pulse from the emitter-follower goes to the inverting input of a high performance operational amplifier such as model A502 manufactured by Intronics Incorporated. This amplifier has a response fast enough to respond to thirty nanosecond pulses. The diode feedback clips negative inputs and allows the circuit to respond only to positive pulses. The AC voltage gain is approximately 3.5 set by feedback resistors 1200 ohms and 560 ohms. The 1 microfarad capacitor with the diode acts as a fast pulse integrator. The DC level developed across the capacitor is buffered by a transistor emitter-follower circuit using an PNP transistor such as MPS6519 manufactured by Motorola. The feedback from the transistor sets the quiescent level of the operational amplifier. Additional gain of two is provided by the output operational amplifier such as model LM747 manufactured by National Semiconductor Corporation.

The output of the peak detector circuit goes to the analog divide circuits shown in FIG. VIII.

The output from the time difference circuits are routed to pulse width integrator and peak detect and hold circuits. One of these circuits is shown in FIG. XXI. Transistor Q1 provides voltage gain to PNP transistor Q2 which is a 2N2907 used as an emitter follower driving the base of another 2N2907. As long as the positive pulse is present, transistor Q3 is turned on which allows capacitor C3 to charge toward the 12 volt supply through resistors R6 and R7 which provide approximately a 0.5 microsecond time constant; therefore, the peak charge on C3 is proportional to the width of the input pulse or the time difference. Transistor Q4 provides the capability of discharging the capacitor through a low resistance path when turned on. The voltage on capacitor C3 goes to the non-inverting input of operational amplifier 747. The positive voltage is peak detected through diode CR2 and capacitor C5 resulting in a voltage level proportional to the input pulse width or time difference. This voltage is then buffered by the following operational amplifier for routing to the analog multiplexer.

The analog multiplexer is a modular circuit such as a model MM8 manufactured by Datel Inc. This circuit provides the capability to time share the analog to digital converter so that all four analog voltages use the same converter. The converter is a general purpose A/D converter such as model 270-3DQZ manufactured by Dynamic Measurements Corporation. Inasmuch as the converter is a commercially available component, it is not shown in detail in the drawings. When the conversion command signal on lead 451 goes high, the A/D convertor outputs are reset and the convertor status line goes high indicating a conversion is in process. The conversion command signal on lead 451 going low starts the conversion which takes a maximum of 36 microseconds. The A/D converter has 12 line binary coded decimal (BCD) output which are connected in parallel fashion (see lines 452A, B, C, and D of FIG. II) to latch and display circuits 453A, B. C, and D. Referring now to FIG. XXIII, latch and display circuit 453A is shown in more detail. Each latch is a 4-bit bistable latch such as SN74L77 manufactured by Texas Instruments Incorporated. The latches are strobed (grated) by the timing control circuitry and 31 via lead 451 (FIGS. II and XXII) at the end of A/D conversion period to place the results of each analog conversion into the selected display as now to be described. The output of each latch goes to a BCD to seven segment decoder 454A. The decoder is a SN7446A manufactured by Texas Instruments Inc. Each decoder output connects to a L.E.D. seven segment display such as model DM3000 manufactured by Datel Systems Inc.

The output of the A to D converter 421 is connected in parallel with the other three displays which are gated sequentially by the timing and control circuitry 31, as previously described.

The trigger pulse to drive the transducer is generated from the A output of the second decode divider. When this signal is high and the C output of the first divider goes high (4 microseconds later), the gate 1 flip-flop (SN7474) is set and gated amplifier number 1 is enabled. A positive signal from gated amplifier 1 rests this flip-flop and sets the gate for amplifier number 2 and so on for number 3. If signals are not received, all flip flops are reset by the combination of A2 low and C1 high in gate 7402.

The display strobe is generated from the output of the series of dividers. The switch allows the strobe sequence to occur once each second, once every two seconds or not to occur so that the display is held.

The conversion command is generated combining the C2 and D2 signals from the decode chain.

While this circuit would have advantages relating to physical compactness of the circuitry entailed, the invention is not to be considered limited to its use. A second embodiment 500 and 600, employing components which may be more readily obtainable from existing commercial sources, will now be described. This embodiment performs essentially the same functions, except that the third reflected pulse is compared to the second reflected pulse rather than the first reflected pulse (a technique which can also be performed using the first circuit embodiment if desired).

As a general summary of the operation of the second embodiment, the sample rate is established by rate oscillator 501 at approx. 10 KHZ. These pulses trigger an initial pulse producer or pulser 502 which excites the transducer 20. The return echos are received by a noise reject and limiter circuit 503 which blocks out any spurious signals, noise, or ringing from the pulser and limits the voltage amplitude of its output, which output is fed into a video frequency preamplifier 504. The preamplifier 504 feeds a variable gain amplifier 506 with a potentiometer controlled, variable gain output. From the variable gain amplifier 506, the video frequency echo signals are fed to three video frequency gated amplifiers 507A, 507B, 507C. The amplifiers 507A, 507B, 507C are gated off until arming circuits in the systems timing circuit 519 (FIG. XIII) gate them on, and off, sequentially.

The gated video echos are then routed to their respective peak detectors 508A, 508B, 508C which convert gated signal amplitude into a corresponding D.C. voltage. These voltage levels are fed to voltage-to-frequency converters 509A, 509B, 509C which transform the D.C. levels into signals of proportionally corresponding frequencies. These frequency signals are then routed to a frequency ratio counter display section 520 having two display devices 511A, 511B (light emitting diodes) which present the ratio of signal amplitudes as a digital display. Arming gates 517A, B, C are connected to a signal detector and pulse width converter section (FIG. XIV).

The (hereinafter pulse width converter 512) (hereinafter pulse width converter 512) establishes two pulses whose width is directly proportional to the time lapse from Signal 1 to Signal 2, and Signal 2 to Signal 3. The pulses are time integrated and converted into a proportional frequency which is counted and displayed as metal and bond thicknesses.

The operation will now be described in detail, and the following terminology has been used hereinafter. "Signal 1" is the first echo received representing the outer surface of the laminated aluminum part being inspected. The interface point between the face of the transducer and the test specimen. "Signal 2" is the second echo received representing the back surface of the first laminate. "Signal 3" is the third echo received representing the top surface of the second laminate. "T1-T2" is the real time period from the positive half cycle peak to Signal 1 to Signal 2. "T2-T3" is the real time period from the positive half cycle peak of Signal 2 to the negative half cycle peak of Signal 3. "Mono" refers to a monostable multivibrator ("one shot"). "UJT" is an abreviation for unijunction transistor. "Pulser" refers to the circuit which produces the initial pulse ("main bang") which electrically excites the transducer crystal element. "CLR" - Clear, the act of setting a flip-flop or monostable to its original stable state (Q = logical 0, Q = logical 1). "Blanking" is a time delay period to disable receiving circuitry from a period before the initial pulse, to a period shortly before the arrival of the first echo, Signal 1. "ARM" refers to a pulse which enables the respective video frequency gated amplifiers 507A, B, C and video timing flip-flops of the pulse width converter section 512. "F1" refers to the proportional frequency of the peak DC value of Signal 1 and "F2 and F3" are the same as F1.

The system's timing circuit 519 (FIG. XIII) includes a UJT transistor 525, which acts as a free running, relaxation oscillator whose frequency can be adjusted by potentiometer 526. NPN transistor 527 serves as an interface pulse amplifier to 528, the blanking trigger monostable. The output of mono 528, line 534, resets the thickness pulse integrators 513A, B at point 529 and 530 (FIG. XIX), and partially enables gate 531A to trigger the sync reset mono 532. The trailing edge of this pulse, point 533 (FIG. XIX), triggers the pulser trigger mono, 535, and the blanking mono, 536. The blanking mono 536 pulse's duration, point 537 (FIG. XIX), inhibits the pulse width converter section 512, as well as resetting the phase comparators section 518. This pulse terminates 400 n.s. before the first echo is received, point 538 (FIG. XIX). The trailing edge of the blanking pulse, point 539 (FIG. XIX), triggers the ARM 1 mono, 540. The ARM 1 output pulse 541 enables the Signal 1 gated video amplifier, section 507A (FIG. IX), and the T1 flip-flop, to be described, located in section 512C (FIG. IX).

When signal 1 is received, the ARM 1 mono 540 is asynchronously reset by the CLR1 flip-flop to be described in section 512 (FIG. IX). As the ARM 1 pulse is terminated point 542 (FIG. XIX), it triggers a 50 n.s. time delay mono, 543, point 545 (FIG. XIX). This insures that the Signal 1 oscillations have ceased when the ARM 2 mono, 544 is triggered. The ARM 2 mono pulse output line 546 enables its respective Signal 2 gated amplifier section 507A (FIG. IX) and T2 flip-flop, to be described, and is reset in the same manner that the ARM 1 mono was. Because the oscillations of Signal 2 are so short, a 50 n.s. time delay mono, identical to 543, is not required. As the ARM 2 pulse terminates, point 547 (FIG. XIX), it triggers the ARM 3 mono, 548. This pulse enables the Signal 3 gated amplifier, section 507B (FIG. IX), whose output, containing an inverted Signal 3, trips the CLR 3 flip-flop, to be described, which in turn resets the ARM 3 mono 548. The metal and bond thickness counters require a known, stable reference which is provided in the form of a 100 m.s. gate pulse 549. Transistors 551, 552, crystal 553 and their associated circuitry 553 form a 100 KHZ crystal controlled oscillator whose output is divided down in division of 10 by decade frequency dividers 554, 555, 556 and 557. 558 is a toggle flip-flop whose output duration is a precision 100 m.s. interval. During this 100 m.s. period, the thickness counters, section 514A and B, FIG. IX, are enabled to count the corresponding thickness frequencies from the pulse width to frequency converters, section 513A and B (FIG. IX). The termination of the 100 m.s. pulse from 558 triggers the strobe mono, 559. It's output pulse, line 562, strobes the latches in the thickness counters, section 514A and B (FIG. IX), which transfer the counter data to their respective decoder-drivers. This pulse on line 560 also is fed back to the toggle flip-flop 558 to clear it, and to transistor 561 which clears the decade dividers, 554, 555, 556 and 557. Upon completion of the strobe pulse, 562, the sync reset gate, 531A, is enabled by toggle flip-flop 563. The next blanking trigger pulse, 534, triggers the sync reset mono, 532. It's output pulse, line 564, feeds back and clears the toggle flip-flop, 563.

With respect now to the gated video frequency amplifier section (507A, B, C), FIG. IX, transistor 565 forms the pulser or initial pulse producer. This circuit is not described in detail, but operates in substantially the same manner as has been previously described with respect to pulse generator circuit 30, FIGS. II and IV, transistor 51 being analogous to pulser transistor 565. Components 567, 568, 569, 570, 571, 572, 574 and 575 form a noise rejection-voltage limiting circuit which operates as follows: In the quiescent state, resistors 567 and 568 form a voltage divider which slightly reverse biases diode 569. Resistor 574 provides a common forward bias current source for diode 570 and diode 571. Resistor 572 provides the ground bias reference for diode 570, as well as determining the pulser circuit 502 output impedance. Resistor 575 provides the ground bias reference for diode 571, as well as determining the input impendence to video frequency preamplifier 504. When transistor 565 triggers, diode 569 becomes forward biased due to the negative pulse coupled by pulser capacitor 566. This pulse is coupled through diode 569 to the transducer output jack 573. Resistor 572 matches transducer impedances. As the potential across resistor 572 becomes negative, diode 571 becomes reversed biased through diode 570 and isolates the input of the video frequency pre-amp, 504, from the high voltage level of the initial pulse. As the initial pulse terminates, diode 569 becomes reversed biased again, isolating any ringing noise caused by pulser transistor 565. The returning echos are now free to enter the video frequency preamplifier 504 input unattenuated through coupling capacitor 576. Video frequency amplifiers 504, 505, 506, 507A, B, C utilize Pin 1 of each for controlling their individual gain. Using Pin 2 as an input in each amplifier, Pin 1 serves as a voltage controlled gain port. With zero volts (ground potential) applied to Pin 1, the full 20 db gain of each amp may be achieved. A + 3V or greater potential on Pin 1 will inhibit any amplification (60 db attenuation) with a near linear response achieved between these two levels (ground and + 3V). Video frequency preamplifier 504 provides a voltage gain of 10 (20 db) utilized as a single ended R.F. video amplifier. R13, 14, C8, 9, 10 and 11 provide power supply A.C. isolation, as all the amplifiers have, except for IC6. The pre-amp non-inverting output, Pin 6, drives the gain amp, IC2, and the video timing output amp, IC6. C11 provides D.C. isolation with R15 serving as an input load resistor. IC2 drives the gated video amplifiers, IC3, 4 and 5. These gated amplifiers are only gated on during the period their respective echos appear. Using IC3 as a typical example, C18 and R22 balance the differential input. R23, 24 and 25 form a voltage divider which allows R24 to provide a positive or negative D.C. offset output voltage during the non-amplifying period of IC3. IC4 and IC5 work identically with the exception of IC5. It's output is inverted. The negative half cycle of signal 3 has a greater peak magnitude than it's positive half cycle. J13 connects to the T3 circuits on the Video Timing Board.

The Video Timing Board, BT-02, circuit converts the period from Signal 1 to Signal 2, and from Signal 2 to Signal 3 to pulses whose pulse width is proportional to the real time lapse between those two sets of signals. This section 512 also generates clearing signals from the ARM monos, section 517A, B and C, (FIG. IX).

Amplifier 580A, B and C are fast responding voltage level comparators. Potentiometer 581A, B and C set D.C. threshold levels and the comparitors respond to positive peaks of the video frequency gated amplifier outputs, section 507A, B, C, FIG. IX. Diodes 581A, B and C and resistors 583A, B, and C provide regenerative feedback to insure a small amount of comparitor input hysterises.

At quiescent, comparitor 580A, output, line 584, is in the high state which saturates inverting transistor, 588, thus inhibiting ARM 1 gate, 589. When Signal 1 appears on input line 590, also shown in FIG. XI, it's positive going half cycle peak is higher than the positive threshold level set by potentiometer 501A. The output of comparitor 580A, line 584, switches low (ground potential) causing transistor 588 to become biased off. The ARM 1 gate, 589, in conjunction with the ARM 1 pulse input lead 541, qualify the gate causing its output, line 591, to go low. This acts sets the T1 – T2 flip-flop 592A and B output, line 593, to the high state, and sets the CLR1 flip-flop 594A and B output, line 595, to the low state. The CLR1 signal lead 595 feeds back to the ARM 1 mono 540, FIG. XIII in section 517A and clears the arm 1 mono (terminates the ARM 1 pulse). This action inhibits the ARM 1 gate, 589, until the next ARM 1 pulse is issued.

When Signal 2 arrives, comparitor 580B, transistor 588B, ARM 2 gate 589B, respond in the same manner, except the T2-T3 flip-flop 596A and B output, 598, goes high with the output from 576B feeding back thru gate 599 and clearing the T1-T2 control flip-flop 592A and B causing line 593 to go low. Thus, the period of Signal 1 to Signal 2 now becomes a pulse at line 593. When Signal 3 arrives, on line 600, also shown in FIG. XI, comparitor 580C, transistor 588C, and ARM 3 gate 589C, respond in the same manner as previously described clearing the T2-T3 control flip-flop 596A and B through gate 602 as well as setting the CLR3 flip-flop 601A and B. Notice the BLKG pulse input, line 577, clears all control flip-flops during the blanking period.

The Thickness Counter Circuit, BT-04, includes the T1-T2, or T2-T3 pulse inters on I/O Pin C. Q2, Q3, R4, 5, 6 and 7, D1 and C3 form a constant current source to charge C3 through D1. Q1 and its associated circuitry form an off-on switch to activate the integrator.

In quiescent, Q1, 2 and 3 are off. Integrating capacitor, C3, is discharged to ground, during the blanking trigger period, by Q4. When the incoming timing pulse arrives, Q1 saturates which in turn turns on Q2, a current amplifier, and Q3 — the constant current source. C3 charges linearly until the input timing pulse goes low. Q1, 2 and 3 then turn off and C3 holds its level of charge. D1 provide D.C. Operational Amplifier 611A, 612A and transistor 616A form a ramp integrator voltage-to-frequency converter. The first half of operational amplifier 611A forms an integrator with the R-C time constant determined by potentiometer 613A, resistor 614A and capacitor 615A. With a positive voltage applied from line 617A from peak detector buffer 610A, the integrators output, line 618, initiates a negative goind linear ramp. The output of operational amplifier 612A, line 619A is negative insuring cut-off of transistor 616A. Resistors 620A and 621A form a voltage divider placing a —4v DC reference level on the non-inverting input of operational amplifier 612A. When the negative going ramp reaches the —4v DC reference level, line 619A of operational amplifier 612A, employed as a reset switch, its output goes positive which forward biases transistor 616A. Transistor 616A then saturates discharging (resetting) capacitor 615A. The emitter of transistor 616A then assumes ground potential. This resets the integrator 611A to begin another cycle. Transistor 622A is biased off until transistor 616A turns on. Emitter follower transistor 623A then removes the reverse bias to transistor 622A through resistor 624A allowing transistor 622A to saturate during the integrator 611A reset period. Gate 625A provides pulse inversion with gate 626A gating the V/F converter pulses for 100 m.s. gate 627A provides inversion again and drives the clock input to thickness counter, 628A. The three digit BCD counters, 628A, 629A, 630A accumulate the thickness count. These counters are strobed by line 562 (also shown in FIG. XIII) and their contents released to the LED displays, section 516A and B (FIG. IX), on the front panel.

Operational amplifiers 632A, 633A, transistors 634A, 635A and 636A form a converter, identical to the V/F converter shown in FIG. XVIII and FIG. IX, used to convert the peak amplitude D.C. levels of Signals 1, 2 and 3 to a corresponding frequency.

Referring now to peak detector section 508A, B and C, FIGS. IX and XIV, operational amplifier 643A and buffer 644A form a high speed peak detector circuit. As the gated video echo signal 1 (one) on input line 640, also shown in FIG. XI, swings positive the output of operational amplifier 643A swings positive on line 645A and charges capacitor 647A through diode 646A. High input impendance unity gain buffer 544A completes the feed-back loop through resistor 650A to the inverting input of operational amplifier 643A. For example, if the positive peak of the input signal reached a maximum of 1.0v, then output line 645A would slow to approx. 1.6v (signal peak plus V$f$ of diode 646A) with 1.0v applied to capacitor 647A and fed back through buffer 644A to the inverting input of operational amplifier 643A. Notice diode 649A is reversed biased during this action.

When the input signal on line 640 swings negative, the feedback loop through buffer 644A is broken due to diode 646A becoming reversed biased. Diode 649A prevents the output of operational amplifier 643A from saturating in the negative direction by clamping the negative output to approx. —0.6v (V$f$ diode 649A). Resistor 650A prevents direct coupling from buffer output line 648A through diode 649A to the non-inverting input of operational amplifier 643A.

Notice the absence of a reset circuit to discharge capacitor 647A after sampling. Due to the very fast peak detector acquisition time required (16 n.s.), the value of capacitor 647A must be small in order to prevent an excessive R-C time lag in charging capacitor 647A within a close value of the input peak. Due to the small value of charge (coulombs) stored in capacitor 647A, discharge of capacitor 647A through minority carriers in diode 646A and the input bias current required by buffer 644A cause capacitor 647A to hold a close D.C. level for approximately 3 m.s. To hold the peak value for digital processing, a minimum of 100 m.s. is required, therefore, a second peak detector circuit, operational amplifiers 651A and 652A are used to charge capacitor 653A to the D.C. level of the output of buffer 644A. Notice that the acquisition time for the second peak detector can be almost 200 times as long which allows the increase value of capacitor 653A to be fully charged and to hold this charge without significant drooping effect within 100 m.s.

When the transducer is lifted away from the specimen, capacitor 653A bleeds off sufficiently to accept a new charge once the transducer is reapplied.

The V/F converter circuit, section 509A (FIG. IX) operates identically to the ones found in sections 513A and B, FIG. IX, and as described in detail with respect to pulse width converter 513A in reference to FIG. XVIII.

The other peak detectors 508B and C, FIG. IX, operate identically as previously described.

The Metal-Bond Ratio Counter, section 510B, FIG. IX, is provided, as shown in FIG. XVII, to display the ratio of Signal 2 peak value to Signal 1 peak value (the equation, (Signal 2 peak/Signal 1 peak) = Ratio, must be processed).

F1 as previously defined as the proportional frequency of the peak D.C. value of Signal 1 enters line 660 as shown on FIG. XVI as a clock pulse to decade divider 661. Three stages of decade division are performed on F1 before it can clock the gate control flip-flop, 664. As the Q output gate control flip-flop 664 assumes the 1 state (high), count control gate, 665, is enabled to pass F2 for 1000 periods of F1. At the completion of this period, control flip-flop 664 is clocked again which inhibits the count control gate, 655, and triggers the strobe mono, 666. The value of the three decade BCD ratio counters 667, 668 and 669 are then released to the digital readout, section 511B, FIG. IX.

At the completion of the strobe pulse from strobe mono 666, toggle flip-flop 670 is clocked, whose output triggers reset mono, 671, and clears control flip-flop 664. Once reset is accomplished, the process repeats itself.

A Bond-Metal Ratio Counter, section 510A, FIG. IX, is also provided, as shown in FIG. XV. This ratio counter operates in an identical manner as the Metal- Bond Ratio Counter, section 510B, FIG. XVII and IX, except F3/F2 ratio is processed.

Phase detector circuits, see FIG. XV, are fast voltage comparitors working in conjunction with amplifiers 680 and 681, gates 682A, B, C, D; 683; 684A, B; 685A, B and C to determine the phase of Signal 1.

The composite video signal is applied to both comparitor through I/O Pin V. During the blanking period, the phase condition flip-flop, IC11-8 and IC9-3, the inhibit ARM 1 flip-flop, IC17-6, are cleared. Note that IC16 will react first on a positive leading edge, and IC15 will react first on a negative leading edge. In a quiescent state, IC9-8 and IC15-7 are low which cause control gates IC9-6 and IC9-11 to be disqualified.

When the ARM1 pulse arrives, one input to both of these control gates becomes qualified (IC9-12 and IC9-4). If the leading half cycle of Signal 1 is positive going, IC16-7 will switch low, inverted to a high through IC9-8, and qualifies control gate IC9-6 which goes low. This action sets IC11-8 to a high, forward biasing Q2 which turns on the red "out of phase" light. IC17-6 goes low during this period inhibiting the ARM1 control gate which locks out further influence by the voltage comparitors. Had the leading half cycle of Signal 1 been negative going, IC15-7 would have reacted first, qualified IC9-11, and latched IC9-3 high (green light on) until the next sample period. D1, R8, D2, R11 provide regenerative feedback to insure a small amount of switching hysterisis. IC13 and 14 process Signal 3 phasing in an identical manner. R10, 14, 27 and 22 adjust the threshold levels of their respective comparitors.

It can now be understood that the present invention, employing either of the above-described embodiments, provides definite advantages over the prior art, not only is a positive indication of good or bad bond provided, but the system also provides an indication of what type of bond fault exist. That is, the display indicates the presence of a porous adhesive, and a "go," "no go" indication of a lack of bonding between the bond layer and the second structure is indicated by the phase reversal indicators. Thicknesses are also displayed, so that the thickness of the adhesive layer is readily apparent. The plastic delay column (used in the optional first embodiment) provides the advantage that proper coupling is more readily apparent from the phase reversal.

While only two embodiments of the invention, together with modifications thereof, have been described in detail herein and shown in the accompanying drawing, it will be evident that various further modifications are possible in the arrangement and construction of its components without departing from the scope of the invention.

What is claimed is:

1. Apparatus for evaluating a bond between first and second structures bonded together by an intermediate layer of adhesive to form a composite construction, the first structure having a first surface and an oppositely facing, second surface having at least partial contact with the layer of adhesive, the second structure having a surface facing the layer of adhesive and having at least partial contact with the layer of adhesive, the apparatus comprising:

means for transmitting a pulse of ultrasonic wave energy, of a wavelength shorter than the thickness of the first structure and shorter than the thickness of the intermediate adhesive layer, the pulse being of a duration at least as short as approximately 1.5 wave cycles, into the first structure and the adhesive layer from a location adjacent the outer face of the first structure and for receiving any subsequent pulses reflected from portions of the composite construction, whereby a first reflected pulse may be reflected from the first surface of the first structure and at least a second reflected pulse may be subsequently reflected from the interface between the first structure and the adhesive layer; and means responsive to the reception, by the pulse transmitting and receiving means, of the first and second reflected pulses, and any third pulse reflected from the interface between the adhesive layer and the second structure, for producing an output signal indicative of effective bonding of the adhesive layer to both structures upon the reception by the pulse transmitting and receiving means of second and third pulses of amplitudes within respective, predetermined ranges.

2. The apparatus of claim 1, comprisng means for indicating the existence of a bond fault upon the ratio between the amplitude of any third reflective pulse and the amplitude of the second reflected pulse being greater than a predetermined value.

3. The apparatus of claim 1, further comprising means for indicating a bond fault upon the second pulse being out of phase with any third pulse reflected from the interface between the adhesive layer and the second structure.

4. The apparatus of claim 1, comprising means for indicating a bond fault upon there being received no third pulse, of at least a predetermined amplitude, reflected from the interface between the adhesive layer and the second structure.

5. The apparatus of claim 1, comprising means for indicating the existence of a bond fault upon the ratio between the amplitude of the second reflected pulse and the amplitude of the first reflective pulse being greater than a predetermined value.

6. The apparatus of claim 1, the means responsive to the reception by the pulse transmitting and receiving means of the first and second reflected pulses and any third pulse reflected from the interface between the adhesive layer and the second structure including: first, second, and third circuit portions and means for conducting input signals to the first, second, and third circuit portions which input signals respectively correspond to the first and second, and any third, reflected pulses received by the pulse transmitting and receiving means, the first, second, and third circuit portions each comprising a means for emitting an output signal corresponding to a received input signal when the respective circuit portion is in an actuated mode and, alternatively, for producing no output signal when the respective circuit portion is in an inhibited mode; and further including timing and control means for sequentially actuating the first and second circuit portions during respective time periods in coincidence with the reception by the pulse transmitting and receiving means of the first and second, reflected pulses and for subsequently actuating the third circuit portion during a time period during which any third reflected pulse may be received.

7. The apparatus of claim 6, wherein the timing and control circuitry means comprises a means for sequentially actuating each of the first, second, and third circuit portions for respective time periods at least as short as the duration of the transmitted pulses of ultrasonic wave energy.

8. The apparatus of claim 6, wherein the timing and control circuitry means comprises a means for inhibiting the first circuit portion during a period subsequent to the reception by the pulse transmitting and receiving means of the first reflected pulse and for inhibiting the second circuit portion during a period subsequent to the reception by the pulse transmitting and receiving means of the second reflected pulse.

9. The apparatus of claim 6, wherein the first, second, and third circuit portions are respective gated amplifiers, the timing and control circuitry means comprising means for sequentially gating the gated amplifiers during time periods corresponding to time periods in which respective ones of the pulses are received.

10. Apparatus for permitting the evaluation of a plurality of properties of a bond between first and second structures formed by an intermediate layer of adhesive to form a composite construction, the first structure having a first surface and an oppositely facing, second surface having at least partial contact with the layer of adhesive, the second structure having a surface facing the layer of adhesive and having at least partial contact with the layer of adhesive, the apparatus comprising:

means for transmitting a pulse of ultrasonic wave energy, of a wavelength shorter than the thickness of the first structure and shorter than the thickness of the intermediate adhesive layer, the pulse being of a duration at least as short as approximately 1.5 wave cycles, into the first structure and the adhesive layer from a location adjacent the outer face of the first structure and for receiving any subsequent pulses reflected from portions of the composite construction, whereby a first reflected pulse may be reflected from the first surface of the first structure and at least a second reflected pulse may be subsequently reflected from the interface between the first structure and the adhesive layer;

means responsive to the reception, by the pulse transmitting and receiving means, of the first and second reflected pulses and any third pulse reflected from the interface between the adhesive layer and the second structure, for producing first, second, and third signals respectively corresponding to the amplitudes of the first, second, and any third reflected pulses, respectively; and means for receiving the first, second, and third signals and for determining the ratio between the amplitudes of the first and second signals and, upon a third pulse being received, for determining the ratio between the third signal and at least one of the first and second signals.

11. Apparatus for permitting the evaluation of a plurality of properties of a bond between first and second structures joined by an intermediate layer of adhesive to form a composite construction, the first structure having a first surface and an oppositely facing, second surface having at least partial contact with the layer of adhesive, the second structure having a surface facing the layer of adhesive and having at least partial contact with the layer of adhesive, the apparatus comprising:

means for transmitting a pulse of ultrasonic wave energy, of a wavelength shorter than the thickness of the first structure and shorter than the thickness of the intermediate adhesive layer, the pulse being of a duration at least as short as approximately 1.5 wave cycles, into the first structure and the adhesive layer from a location adjacent the outer face of the first structure and for receiving any subsequent pulses reflected from portions of the composite construction, whereby a first reflected pulse may be reflected from the first surface of the first structure and at least a second reflected pulse may be subsequently reflected from the interface between the first structure and the adhesive layer; and means responsive to the reception, by the pulse transmitting and receiving means, of the first and second reflected pulses and any third pulse reflected from the interface between the adhesive layer and the second structure, for determining the ratio between the amplitudes of at least two of the first, second, and third reflected pulses.

12. The apparatus of claim 11, comprising means for permitting evaluation of the bond strength by providing an output signal indicative of the ratio between the amplitude of any third reflective pulse and the amplitude of the second reflective pulse.

13. The apparatus of claim 12, comprising means for indicating the existence of a bond deficiency upon the ratio of the amplitude of any third reflective pulse and the amplitude of the second reflective pulse being greater than a predetermined value.

14. The apparatus of claim 11, further comprising means for indicating a bond fault by indicating that the second pulse is out of phase with any third pulse reflected from the interface between the adhesive layer and the second structure.

15. The apparatus of claim 14, comprising means for permitting the determination of a bond deficiency by providing a further indication that the third pulse is of a relatively low amplitude in comparison to one of the amplitudes of the first and second pulse.

16. The apparatus of claim 11, comprising means for indicating the existence of a bond deficiency upon there being received no third pulse, of at least a predetermined amplitude, reflected from the interface between the adhesive layer and the second structure.

17. The apparatus of claim 11, comprising means for indicating the existence of a bond deficiency upon the ratio between the amplitude of the second reflected pulse and the amplitude of the first reflective pulse being greater than a predetermined value.

18. A method of evaluating a bond between first and second structures joined by an intermediate layer of adhesive and forming a composite construction, the first structure having a first surface and an oppositely facing, second surface having at least partial contact with the layer of adhesive, the second structure having a surface facing the layer of adhesive and having at least partial contact with the layer of adhesive, the method comprising:

transmitting a pulse of ultrasonic wave energy, of a wavelength shorter than the thickness of the first structure and shorter than the thickness of the intermediate adhesive layer, the pulse being of a duration at least as short as approximately 1.5 wave cycles, into the first structure and the adhesive layer from a location adjacent the outer face of the first structure and receiving any subsequent pulses reflected from portions of the composite construction, whereby a first reflected pulse may be reflected from the first surface of the first structure and at least a second reflected pulse may be subsequently reflected from the interface between the first structure and the adhesive layer; and generating respective signals in response to the reception, by the pulse transmitting and receiving means, of the first and second reflected pulses, and any third pulse reflected from the interface between the adhesive layer and the second structure; and determining the ratio between the first and second signals and, upon a third pulse being received determining the ratio between the third signal and at least one of the first and second signals.

19. The method of claim 18, further comprising the step of indicating the existence of a bond deficiency upon the ratio between the amplitude of the third signal and the amplitude of the second signal being greater than a predetermined value.

20. The method of claim 18, further comprising the step of providing an indication of a bond fault upon the second pulse being out of phase with any third pulse reflected from the interface between the adhesive layer and the second structure.

21. The method of claim 18, further comprising the step of indicating a bond deficiency by indicating that no third pulse, of at least a predetermined amplitude is reflected from the interface between the adhesive layer and the second structure.

22. The method of claim 18, comprising the step of indicating the existence of a bond deficiency by providing an indication that the ratio between the amplitude of the second reflected pulse and the amplitude of the first reflective pulse is greater than a predetermined value.

* * * * *